United States Patent [19]

Petersen

[11] Patent Number: 4,555,261
[45] Date of Patent: Nov. 26, 1985

[54] HERBICIDAL SULFONAMIDES

[75] Inventor: Wallace C. Petersen, Hockessin, Del.

[73] Assignee: E. I. Du Pont de Nemours and Company, Wilmington, Del.

[21] Appl. No.: 667,470

[22] Filed: Nov. 1, 1984

Related U.S. Application Data

[60] Division of Ser. No. 395,781, Jul. 12, 1982, Pat. No. 4,491,467, which is a continuation-in-part of Ser. No. 295,247, Aug. 24, 1981, abandoned.

[51] Int. Cl.$^4$ .................. C07D 401/12; C07D 405/12; A01N 43/70; A01N 43/66

[52] U.S. Cl. .......................................... 71/90; 71/93; 544/207; 544/209; 544/212; 544/2; 544/3; 544/8; 544/54; 544/58.6; 544/63; 544/66; 544/67; 544/96; 544/98

[58] Field of Search ...................... 71/93, 90; 544/207, 544/209, 212, 2, 3, 8, 54, 58.6, 63, 66, 67, 96, 98

[56] References Cited

U.S. PATENT DOCUMENTS 4,383,113 5/1983 Levitt .................................. 544/212

FOREIGN PATENT DOCUMENTS 0007687 5/1979 European Pat. Off. .

Primary Examiner—John M. Ford

[57] ABSTRACT

This invention relates to a novel class of sulfonamides and their use as herbicides and plant growth regulants.

17 Claims, No Drawings

HERBICIDAL SULFONAMIDES

This application is a divisional application of application Ser. No. 395,781, filed July 12, 1982, now U.S. Pat. No. 4,491,467, which in turn is a continuation-in-part of application Ser. No. 295,247, filed Aug. 24, 1981, now abandoned.

BACKGROUND OF THE INVENTION

This invention relates to a novel class of sulfonamides and their use as herbicides and plant growth regulators.

U.S. Pat. No. 4,127,405 teaches compounds which are useful for controlling weeds in wheat having the formula:

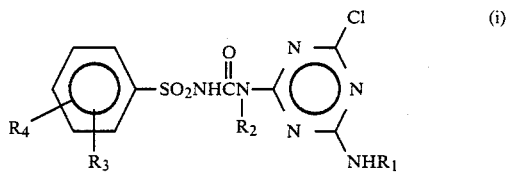

wherein
R₁ is

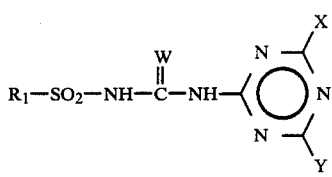

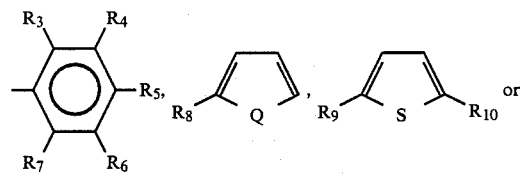

R$_3$ and R$_6$ are independently hydrogen, fluorine, chlorine, bromine, iodine, alkyl of 1-4 carbon atoms, alkoxy of 1-4 carbon atoms, nitro, trifluoromethyl, cyano, CH$_3$S(O)$_n$— or CH$_3$CH$_2$S(O)$_n$—;

R$_4$ is hydrogen, fluorine, chlorine, bromine or methyl;

R$_5$ is hydrogen, fluorine, chlorine, bromine, methyl or methoxy;

R$_7$ is hydrogen, fluorine, chlorine, bromine, alkyl of 1-2 carbon atoms or alkoxy of 1-2 carbon atom;

R$_8$ is hydrogen, methyl, chlorine or bromine;

R$_9$ and R$_{10}$ are independently hydrogen, methyl, chlorine or bromine;

W and Q are independently oxygen or sulfur;

n is 0, 1 or 2;

X is hydrogen, chlorine, bromine, methyl, ethyl, alkoxy of 1-3 carbon atoms, trifluoromethyl, CH$_3$S— or CH$_3$OCH$_2$—; and Y is methyl or methoxy; or their agriculturally suitable salts; provided that:

(a) when R$_5$ is other than hydrogen, at least one of R$_3$, R$_4$, R$_6$ and R$_7$ is other than hydrogen and at least two of R$_3$, R$_4$, R$_6$ and R$_7$ must be hydrogen;

(b) when R$_5$ is hydrogen and all of R$_3$, R$_4$, R$_6$ and R$_7$ are other than hydrogen, then all of R$_3$, R$_4$, R$_6$ and R$_7$ must be either chlorine or methyl; and (c) when R$_3$ and R$_7$ are both hydrogen, at least one of R$_4$, R$_5$ or R$_6$ must be hydrogen.

Netherlands Pat. No. 121,788, published Sept. 15, 1966, discloses the preparation of compounds of the following Formula and their use as general or selective herbicides:

wherein
R$_1$ and R$_2$ may independently be alkyl of 1-4 carbon atoms; and

R$_3$ and R$_4$ may independently be hydrogen, chlorine or alkyl of 1-4 carbon atoms.

U.S. Pat. No. 3,637,366 discloses compounds having the formula:

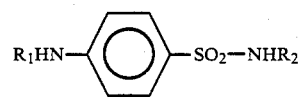

wherein
R$_1$ is hydrogen or lower saturated aliphatic acyl; and
R$_2$ is hydrogen, 2-pyrimidinyl, pyridyl, amidino, acetyl or carbamoyl.

The disclosed compounds are said to provide control of crabgrass, cress, endive, closer and *Poa annua*.

French Pat. No. 1,468,747 discloses the following para-substituted phenylsulfonamides, useful as antidiabetic agents:

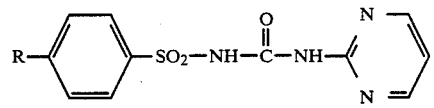

wherein R=H, halogen, CF$_3$ or alkyl.

Logemann et al., Chem. Ab., 53, 18052g (1959), disclose a number of sulfonamides, including uracil derivatives and those having the formula:

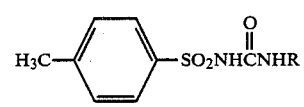

wherein R is butyl, phenyl or

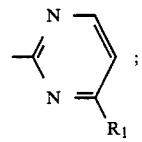

and R$_1$ is hydrogen or methyl. When tested for hypoglycemic effect in rats (oral doses of 25 mg/100 g), the compounds in which R is butyl and phenyl were most potent. The others were of low potency or inactive.

Wojciechowski, J. Acta. Polon. Pharm. 19, p. 121-5 (1962) [Chem. Ab., 59 1633 e] describes the synthesis of N-[(2,6-dimethoxypyrimidin-4-yl)aminocarbonyl]-4-methylbenzenesulfonamide:

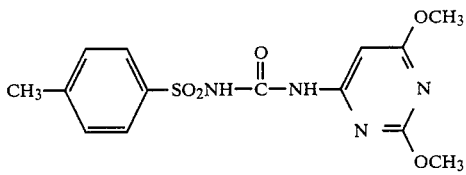

Based upon similarity to a known compound, the author predicted hypoglycemic activity for the foregoing compound.

Substituted-pyrimidinyl sulfonylureas of the following formula, which are also para-substituted on the phenyl ring, are disclosed in Farmco Ed. Sci., 12, 586 (1957) [Chem. Ab., 53, 18052 g (1959)]:

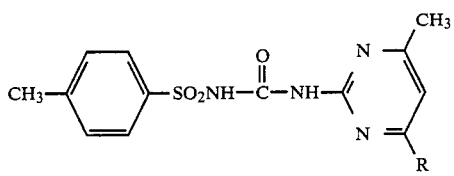

wherein R=H or $CH_3$.

Unexamined European Pat. No. 7687 discloses, among others, herbicidal sulfonylures of the general structure:

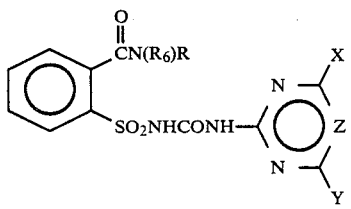

where
R is H, alkyl, alkenyl, aryl, etc.;
$R_6$ is H or alkyl; or
R and $R_6$ can be taken together to form $-(CH_2)_4-$, $-(CH_2)_5-$, $-(CH_2)_6-$, $-CH_2CH_2OCH_2CH_2-$ or $-CH_2CH_2N(CH_3)CH_2CH_2-$.

U.S. Ser. No. 209,307, filed Nov. 24, 1980, discloses, among others, herbicidal sulfonylureas of the general structure:

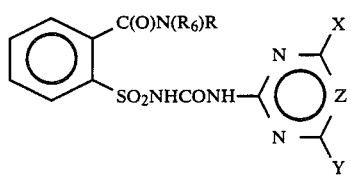

where
R is as disclosed in U.S. Ser. No. 029,281, now abandoned; and
$R_6$ is

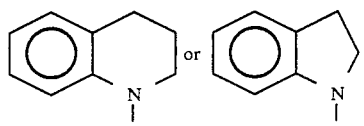

The presence of undesired vegetation causes substantial damage to useful crops, especially agricultural products that satisfy man's basic food and fiber needs, such as cotton, rice, corn, wheat, and the like. The current population explosion and concomitant world food shortage demand improvements in the efficiency of producing these crops. Prevention or minimizing the loss of a portion of valuable crops by killing, or inhibiting the growth of undesired vegetation is one way of improving this efficiency. A wide variety of materials useful for killing, or inhibiting (controlling) the growth of undesired vegetation is available; such materials are commonly referred to as herbicides. The need still exists however, for more effective herbicides.

SUMMARY OF THE INVENTION

This invention relates to compounds of Formula I and their agriculturally suitable salts, suitable agricultural compositions containing them and their method of use as general and/or selective pre-emergence and/or post-emergence herbicides and as plant growth regulants:

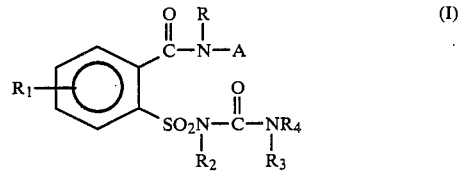

(I)

wherein
A is a five- or six-membered aromatic heterocycle, a five- or six-membered dihydroaromatic heterocycle or a six-membered tetrahydroaromatic heterocycle which contains 1-4 heteroatoms selected from 0-1 oxygen atoms, 0-1 sulfur atoms, and/or 0-4 nitrogen atoms; the heterocycles may be optionally substituted with 1-4 $CH_3$, 1-2 $OCH_3$, 0-1 $SCH_3$, 0-1 Cl, 0-1 $N(CH_3)_2$, or 0-1 CN groups;
R is H or $CH_3$;
$R_1$ is H, F, Cl, Br, $CH_3$, $OCH_3$, $CF_3$ or $NO_2$;
$R_2$ is H or $CH_3$;
$R_3$ is H or $CH_3$;
$R_4$ is

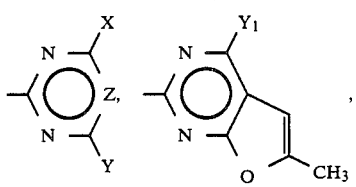

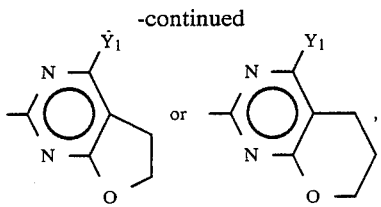

X is CH₃, OCH₃ or Cl;
Y is H, CH₃, C₂H₅, OCH₃, OC₂H₅, CH₂OCH₃, NH₂, NHCH₃ or N(CH₃)₂;
Y₁ is H, Cl, CH₃ or OCH₃; and
Z is CH, CCH₃ or N
provided that (1) the bond between N—R and A is attached to a nitrogen or carbon atom of A;

(2) when A is a thiophene or furan ring, the bond between NR and A is not at the 2- or 5-position of the heterocycle; and (3) when X is Cl, then Z is CH and Y is CH₃, OCH₃, NH₂, NHCH₃ or N(CH₃)₂.

Preferred for higher herbicidal activity and/or more favorable ease of synthesis are:

(1) Compounds of Formula I wherein A is an unsubstituted or substituted six-membered aromatic heterocycle containing one to three nitrogen atoms;

(2) Compounds of Formula I wherein A is an unsubstituted or substituted six-membered dihydroaromatic heterocycle containing two nitrogen atoms;

(3) Compounds of Formula I wherein A is an unsubstituted or substituted five-membered aromatic heterocycle containing one to four nitrogen atoms;

(4) Compounds of Formula I wherein A is an unsubstituted or substituted five-membered aromatic heterocycle containing one or two nitrogen atoms and one oxygen or one sulfur atom;

(5) Compounds of Formula I wherein A is an unsubstituted or substituted five-membered aromatic heterocycle containing one oxygen or one sulfur atom;

(6) Compounds of Formula I wherein A is an unsubstituted or substituted five-membered dihydroaromatic heterocycle containing one nitrogen atom and optionally one heteroatom selected from nitrogen, oxygen or sulfur;

(7) Compounds of Formula I wherein A is an unsubstituted or substituted six-membered tetrahydroaromatic heterocycle containing one nitrogen atom and optionally one heteroatom selected from nitrogen, oxygen or sulfur;

(8) Compounds of Preferred (1)–(7) wherein

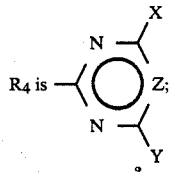

Y is CH₃ or OCH₃; and
Z is CH or N;

(9) Compounds of Preferred (8) wherein A is unsubstituted or optionally substituted with 0–4 CH₃ or 0–2 OCH₃ groups;

(10) Compounds of Preferred (9) wherein A is a pyridine, a pyrimidine or a 1,3,5-triazine;

(11) Compounds of Preferred (9) wherein A is a pyrrole, an imidazole, a pyrazole, or a 1,2,4-triazole;

(12) Compounds of Preferred (9) wherein A is an isoxazole, an oxazole, a 1,3,4-oxadiazole, a thiazole, a 1,2,3-thiadiazole, or a 1,3,4-thiadiazole;

(13) Compounds of Preferred (9) wherein A is a 4,5-dihydroimidazole, a 4,5-dihydroisoxazole, a 4,5-dihydrooxazole, a 4,5-dihydropyrazole, or a 4,5-dihydrothiazole;

(14) Compounds of Preferred (9) wherein A is a tetrahydropyrimidine, a tetrahydro-1,2,-oxazine, a tetrahydrol,3-oxazine, or a tetrahydro-1,3-thiazine;

(15) Compounds of Preferred (10)–(14) wherein R, R₁, R₂ and R₃ are H, and A is unsubstituted, or, optionally substituted with one methyl group.

Specifically Preferred for highest herbicidal activity and/or most favorable ease of synthesis are:

2-[[(4,6-dimethoxypyrimidin-2-yl)aminocarbonyl]aminosulfonyl]-N-(4,6-dimethylpyrimidin-2-yl)benzamide, m.p. 198°–199°;

2-[[(4-methoxy-6-methylpyrimidin-2-yl)aminocarbonyl]aminosulfonyl]-N-(2-pyridinyl)benzamide, m.p. 206°–207°;

2-[[(4,6-dimethylpyrimidin-2-yl)aminocarbonyl]aminocarbonyl]-N-(1,2,4-triazol-3-yl)benzamide, m.p. 226°–230°;

2-[[(4-methoxy-6-methyl-1,3,5-triazin-2-yl)aminocarbonyl]aminosulfonyl]-N-(1-methyl-1H-pyrazol-3-yl)benzamide, m.p. 194°–197°;

2-[[(4-methoxy-6-methylpyrimidin-2-yl)aminocarbonyl]aminosulfonyl]-N-(thiazol-2-yl)benzamide, m.p. 185°–187°;

2-[[(4-methoxy-6-methylpyrimidin-2-yl)aminocarbonyl]aminosulfonyl]-N-(1,3,4-thiadiazol-2-yl)benzamide, m.p. 172°–173°;

N-(3,4-dimethylisoxazol-5-yl)-2-[[(4,6-dimethylpyrimidin-2-yl)aminocarbonyl]aminosulfonyl]benzamide, m.p. 149°–151°.

Synthesis

The compounds of Formula I can be prepared from the corresponding esters by reaction with the heterocyclic amine III in the presence of an equivalent amount of trimethylaluminum according to Equation 1.

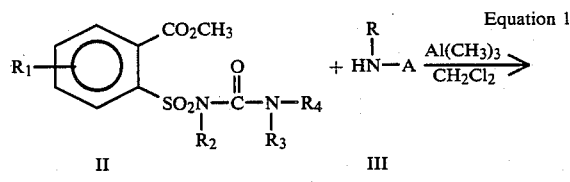

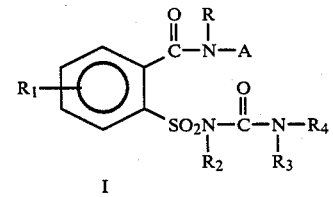

According to the procedure of A. Basha, M. Lipton, and S. W. Weinreb, *Tetrahedron Letters*, 4171 (1977), the heterocyclic amine and the trimethylaluminum are mixed in methylene chloride, followed by the addition of a methyl ester of Formula II. The mixture is then heated at reflux for 12 to 24 hours.

The product can be isolated by addition of aqueous hydrochloric acid to decompose and dissolve the aluminum complexes and salts. Direct filtration of the precipitate or separation of the methylene chloride phase followed by evaporation yields the desired product which may be purified by crystallization or column chromatography.

The preparation of esters of Formula II is described in European Patent Application No. 7687.

Agriculturally suitable salts of compounds of Formula I are also useful herbicides and can be prepared in a number of ways known to the art. For example, metal salts can be made by treating compounds of Formula I with a solution of an alkali or alkaline earth metal salt having a sufficiently basic anion (e.g. hydroxide, alkoxide, carbonate or hydride) quaternary amine salts can be made by similar techniques. Detailed examples of such techniques are given in U.S. Pat. No. 4,127,405, the disclosure of which is herein incorporated by reference.

The compounds of this invention and their preparaton are further illustrated by the following examples wherein temperatures are given in degrees centigrade and all parts are by weight unless otherwise indicated.

EXAMPLE 1

2-[[(4,6-dimethoxypyrimidin-2-yl)aminocarbonyl]aminosulfonyl]-N-(4,6-dimethylpyrimidin-2-yl)benzamide To 1.44 g of trimethylaluminum (10 ml of a 2M solution of trimethylaluminum in toluene) in 100 ml of methylene chloride was added 2.5 g of 2-amino-4,6-dimethylpyrimidine with stirring at ambient temperature. To this mixture was added 4.0 g of N-[(4,6-dimethoxypyrimidin-2-yl)aminocarbonyl]-2-methoxycarbonylbenzenesulfonamide and the solution refluxed for 18 hours. The reaction mixture was then treated with aqueous hydrochloric acid and the precipitated product was found to be nearly pure by thin layer chromatography (TLC) on silica gel with an eluting solvent of ethyl acetate. Trituration of the solid with methylene chloride resulted in pure product (1.8 g); m.p. 198°–199° C.; IR: 3200 cm$^{-1}$, NH, 1720 cm$^{-1}$ sulfonylurea carbonyl, 1700 cm$^{-1}$ amide carbonyl.

NMR: 2.2 ppm s, 6H, CH$_3$ on pyrimidine, 3.9 ppm s, 6H, OCH$_3$ on pyrimidine, 5.8 ppm, s, 1H proton in 5-position on the dimethoxypyrimidine, 6.7 ppm s, 1H, proton in 5-position of dimethylpyrimidine, 7.4–7.8 ppm and 8.0–8.4 ppm M, 4H, aromatic protons.

EXAMPLE 2

2-[[(4-methoxy-6-methylpyrimidin-2-yl)aminocarbonyl]aminosulfonyl]-N-(2-pyridinyl)benzamide To a slurry of 4.0 g of N-[(4-methoxy-6-methylpyrimidin-2-yl)aminocarbonyl]-2-methoxycarbonylbenzenesulfonamide in 100 ml of methylene chloride was added by syringe 10 of a 2M solution of trimethylaluminum in toluene (1.44 g of Al(CH$_3$)$_3$). Evolution of methane gas was seen and the solution became homogeneous. 2-Aminopyrimidine (1.9 g) was then added and the mixture was heated at reflux for 18 hours. The reaction mixture was then treated with aqueous hydrochloric acid and the precipitated product was purified by trituration in methylene chloride, 1.35 g, m.p. 206°–207° C., IR: 1710 cm$^{-1}$ sulfonylurea carbonyl, 1680 cm$^{-1}$ amide carbonyl.

NMR: in TFA, 2.8 ppm, CH$_3$ on pyrimidine, 4.3 ppm, OCH$_3$ on pyrimidine, 6.8 ppm, proton in 5-position of pyrimidine, 7.8–8.0 ppm and 8.4–8.6 ppm, aromatic protons.

EXAMPLE 3

2-[[(4-methoxy-6-methyl-1,3,5-triazin-2-yl)aminocarbonyl]aminosulfonyl]-N-(1,2,4-triazol-3-yl)benzamide To a slurry of 4.0 g of N-[(4-methoxy-6-methyl-1,3,5-triazin-2-yl)aminocarbonyl]-2-methoxycarbonylbenzenesulfonamide in 100 ml of methylene chloride was added by syringe 10 ml of a 2M solution of trimethylaluminum in toluene (1.44 g of Al(CH$_3$)$_3$). Evolution of methane gas was seen. 3-Amino-1,2,4-triazole (1.7 g) was then added and the mixture was heated at reflux for 18 hours. The reaction mixture was then treated with aqueous hydrochloric acid and the precipitated product was purified by trituration in methylene chloride, 0.63 g, m.p. 176°–179° C. NMR in TFA 2.9 ppm s, CH$_3$ on triazine, 4.4 ppm s, OCH$_3$ on triazine, 7.8–8.0 ppm and 8.2–8.5 ppm M, aromatic.

EXAMPLE 4

2-[[(4-methoxy-6-methylpyrimidin-2-yl)aminocarbonyl]aminosulfonyl]-N-(thiazol-2-yl)benzamide To a solution of 2-aminotriazole (2.1 g) in 100 ml of methylene chloride was added 10 ml of a 2M solution in toluene of trimethylaluminum (1.44 g of Al(CH$_3$)$_3$) by syringe. Evolution of methane gas was seen and the solution became homogeneous. To this mixture was added 4.0 g of N-[(4-methoxy-6-methylpyrimidin-2-yl)aminocarbonyl]-2-methoxycarbonylbenzenesulfonamide and the homogeneous solution was heated at reflux for 18 hours. The reaction mixture was then heated with aqueous hydrochloric acid and the precipitated product isolated by filtration, 1.42 g, m.p. 185°–187° C. IR: 1690 cm$^{-1}$ and 1700 cm$^{-1}$ unresolved double carbonyl, NMR: in TFA 2.7 ppm s, CH$_3$ pyrimidine, 4.2 ppm s, OCH$_3$ on pyrimidine, 6.7 ppm s, proton in 5-position on pyrimidine, 7.8–8.0 ppm and 8.4–8.5 ppm M, aromatic, 7.6, 7.7 ppm D, thiazole.

EXAMPLE 5

2-[[(4-methoxy-6-methylpyrimidin-2-yl)aminocarbonyl]aminosulfonyl]-N-(1,3,4-thiadiazol-2-yl)benzamide To a solution of 2-amino-1,3,4-thiadiazole (2.1 g) in 100 ml of methylene chloride was added 10 ml of a 2M solution in toluene of trimethylaluminum (1.44 g of Al(CH$_3$)$_3$) by syringe. Evolution of methane gas was seen from the homogeneous solution. To this mixture was added 4.0 g of N-[(4-methoxy-6-methylpyrimidin-2-yl)aminocarboyl]-2-methoxycarbonylbenzenesulfonamide and the slurry was heated at reflux for 18 hours. The reaction mixture was then heated with aqueous hydrochloric acid and the precipitated product was purified by trituration in methylene chloride, 1.61 g, m.p. 172°–173° C. IR: 1700 cm$^{-1}$ unresolved carbonyls, NMR: in TFA 2.9 ppm s, CH$_3$ pyrimidine, 4.4ppm s, OCH$_3$ on pyrimidine, 5.4 ppm s, thiadiazole, 6.9 ppm s, proton in 5-position on pyrimidine, 8.1 and 8.5 ppm M, aromatic.

Using the procedures and examples described above and choosing the appropriate compounds of Formulae II and III (as illustrated in Table I), the compounds described in Tables II–VII may be prepared.

TABLE I
A: Structures
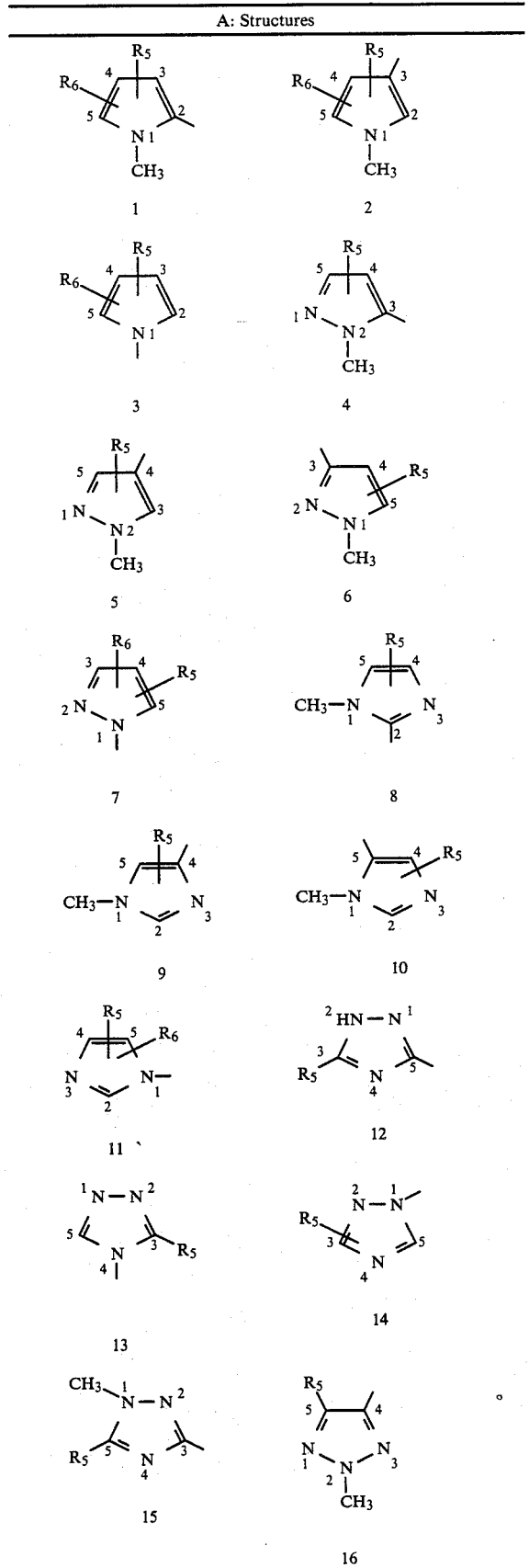
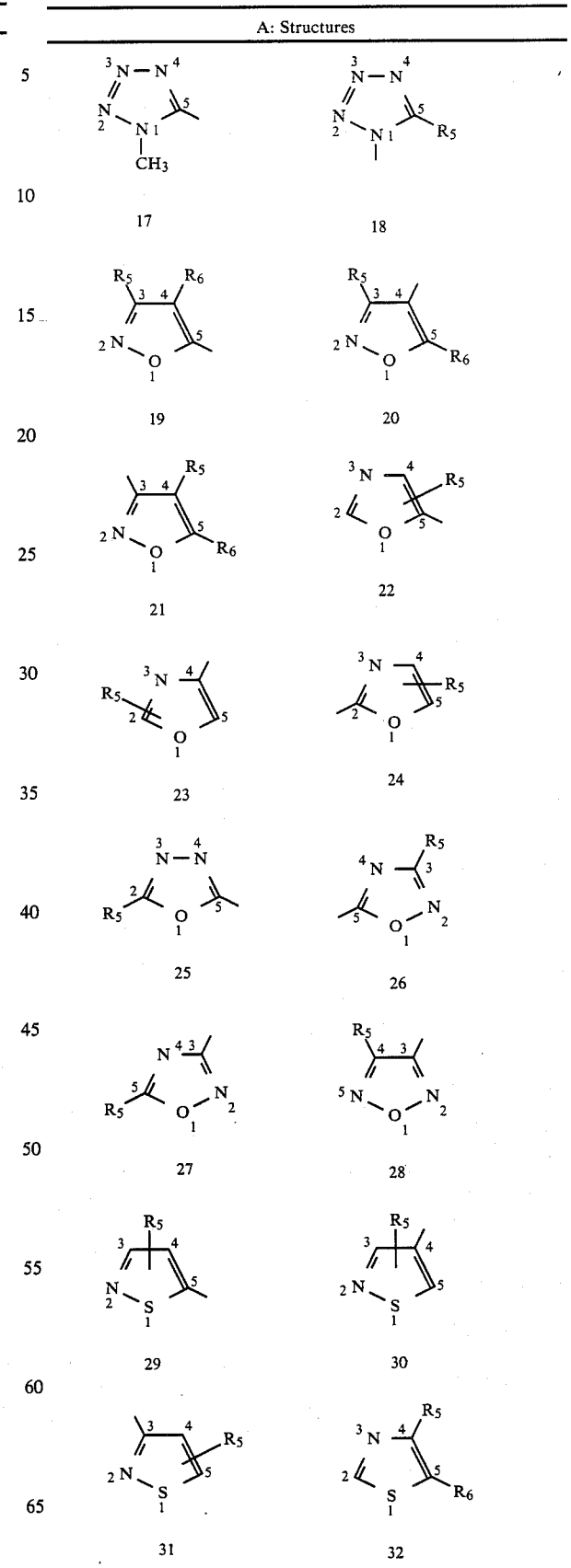

TABLE I-continued
A: Structures (Structures 33–64 depicting heterocyclic ring systems with numbered ring atoms and substituents R₅, R₆.)

TABLE I-continued
A: Structures

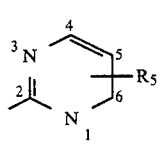
65

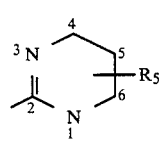
66

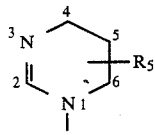
67

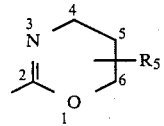
68

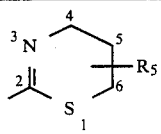
69

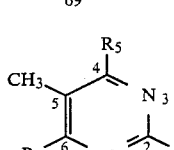
70

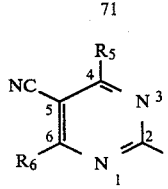
71

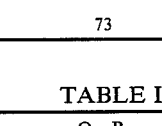
72

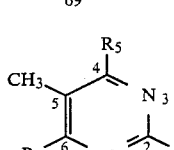
73

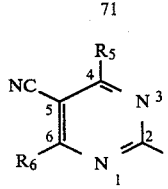
74

TABLE II

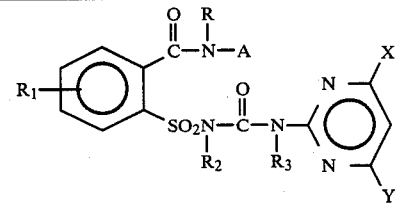

| A | R | R₁ | R₂ | R₃ | R₅ | R₆ | X | Y | m.p.(°C.) |
|---|---|---|---|---|---|---|---|---|---|
| 1 | H | H | H | H | H | H | CH₃ | CH₃ | |
| 1 | H | H | H | H | 4-CH₃ | H | CH₃ | CH₃ | |
| 2 | H | H | H | H | H | H | CH₃ | OCH₃ | |
| 2 | H | H | H | H | 5-CH₃ | H | CH₃ | CH₃ | |
| 3 | H | H | H | H | 2-CH₃ | 5-CH₃ | CH₃ | OCH₃ | |
| 3 | H | H | H | H | H | H | CH₃ | OCH₃ | |
| 4 | H | H | H | H | H | H | OCH₃ | OCH₃ | |
| 5 | H | H | H | H | H | H | CH₃ | OCH₃ | |
| 5 | H | 5-Cl | H | H | H | H | OCH₃ | OCH₃ | |
| 6 | H | H | H | H | H | H | CH₃ | CH₃ | 208–211 |
| 6 | H | H | H | H | H | H | CH₃ | OCH₃ | 203–206 |
| 7 | H | H | H | H | 3-CH₃ | 4-CH₃ | CH₃ | CH₃ | |
| 8 | H | 5-F | H | H | H | H | OCH₃ | OCH₃ | |
| 8 | H | 5-Br | H | H | 4-CH₃ | H | CH₃ | OCH₃ | |
| 9 | H | H | H | H | H | H | CH₃ | CH₃ | |
| 10 | H | H | H | H | H | H | CH₃ | OCH₃ | |
| 11 | H | H | H | H | H | H | OCH₃ | OCH₃ | |
| 12 | H | H | H | H | 5-SCH₃ | — | CH₃ | CH₃ | |
| 12 | H | H | H | H | 5-CH₃ | — | CH₃ | OCH₃ | |
| 12 | H | H | H | H | H | — | CH₃ | CH₃ | 226–230 |
| 12 | H | H | H | H | H | — | CH₃ | OCH₃ | 180–182 |
| 13 | H | H | H | H | 3-CH₃ | — | OCH₃ | OCH₃ | |
| 14 | H | H | H | H | 3-CH₃ | — | CH₃ | CH₃ | |
| 15 | H | H | H | H | H | — | CH₃ | CH₃ | |
| 15 | H | H | H | H | CH₃ | — | OCH₃ | OCH₃ | |
| 16 | H | H | H | H | H | — | CH₃ | OCH₃ | |
| 17 | H | 5-F | H | H | — | — | CH₃ | CH₃ | |
| 18 | H | H | H | H | CH₃ | — | OCH₃ | CH₃ | |
| 19 | H | H | H | H | CH₃ | CH₃ | CH₃ | CH₃ | 149–151 |
| 19 | H | H | H | H | CH₃ | CH₃ | CH₃ | OCH₃ | 173–175 |
| 20 | H | H | H | H | H | H | CH₃ | CH₃ | |
| 21 | H | 5-OCH₃ | H | H | H | H | OCH₃ | OCH₃ | |
| 22 | H | 5-CF₃ | H | H | H | H | CH₃ | CH₃ | |
| 22 | H | 5-NO₂ | H | H | H | — | CH₃ | OCH₃ | |
| 23 | H | H | H | H | H | — | OCH₃ | OCH₃ | |

TABLE II-continued

| A | R | R₁ | R₂ | R₃ | R₅ | R₆ | X | Y | m.p.(°C.) |
|---|---|---|---|---|---|---|---|---|---|
| 24 | H | H | H | H | 5-CH₃ | — | CH₃ | CH₃ | |
| 25 | H | H | H | H | H | — | CH₃ | CH₃ | |
| 25 | H | H | H | H | CH₃ | — | CH₃ | OCH₃ | |
| 26 | H | H | H | H | H | — | CH₃ | CH₃ | |
| 27 | H | 5-NO₂ | H | H | H | — | OCH₃ | OCH₃ | |
| 28 | H | H | H | H | H | — | CH₃ | OCH₃ | |
| 29 | H | H | H | H | H | — | CH₃ | CH₃ | |
| 29 | H | H | H | H | H | — | CH₃ | OCH₃ | |
| 29 | H | H | H | H | H | — | OCH₃ | OCH₃ | |
| 30 | H | H | H | H | H | — | CH₃ | CH₃ | |
| 31 | H | 5-Cl | H | H | H | — | CH₃ | CH₃ | |
| 31 | H | H | H | H | H | — | CH₃ | OCH₃ | |
| 31 | H | H | H | H | H | — | OCH₃ | OCH₃ | |
| 32 | H | H | H | H | H | H | CH₃ | CH₃ | 192–194 |
| 32 | H | H | H | H | H | H | CH₃ | OCH₃ | 185–187 |
| 32 | H | H | H | H | 4-CH₃ | H | OCH₃ | OCH₃ | |
| 32 | H | H | H | H | H | H | OCH₃ | OCH₃ | |
| 33 | H | H | H | H | H | — | CH₃ | CH₃ | |
| 33 | H | H | H | H | H | — | CH₃ | OCH₃ | |
| 33 | H | H | H | H | 2-CH₃ | — | OCH₃ | OCH₃ | |
| 34 | H | H | H | H | 2-CH₃ | — | CH₃ | OCH₃ | |
| 34 | H | H | H | H | H | — | OCH₃ | OCH₃ | |
| 34 | H | H | H | H | H | — | CH₃ | CH₃ | |
| 35 | H | H | H | H | H | — | CH₃ | CH₃ | 168–170 |
| 35 | H | H | H | H | 5-CH₃ | — | CH₃ | OCH₃ | |
| 35 | H | H | H | H | H | — | CH₃ | OCH₃ | 172–173 |
| 35 | CH₃ | H | H | H | H | — | OCH₃ | OCH₃ | |
| 35 | H | H | CH₃ | H | H | — | OCH₃ | OCH₃ | |
| 35 | H | H | H | CH₃ | H | — | OCH₃ | OCH₃ | |
| 36 | H | H | H | H | H | — | CH₃ | CH₃ | |
| 36 | H | H | H | H | H | — | CH₃ | OCH₃ | |
| 36 | H | H | H | H | H | — | OCH₃ | OCH₃ | |
| 37 | H | H | H | H | H | — | CH₃ | CH₃ | |
| 37 | H | H | H | H | H | — | CH₃ | OCH₃ | |
| 37 | H | H | H | H | H | — | OCH₃ | OCH₃ | |
| 38 | H | H | H | H | H | — | OCH₃ | OCH₃ | |
| 38 | H | H | H | H | CH₃ | — | CH₃ | OCH₃ | |
| 39 | H | H | H | H | H | — | CH₃ | CH₃ | |
| 39 | H | H | H | H | H | — | CH₃ | OCH₃ | |
| 40 | H | H | H | H | H | — | CH₃ | CH₃ | |
| 40 | H | H | H | H | H | — | CH₃ | OCH₃ | |
| 41 | H | H | H | H | 4-Cl | — | CH₃ | CH₃ | |
| 41 | H | H | H | H | 4-CN | — | OCH₃ | CH₃ | |
| 41 | H | H | H | H | H | — | CH₃ | CH₃ | |
| 41 | H | H | H | H | H | — | CH₃ | OCH₃ | |
| 41 | H | H | H | H | H | — | OCH₃ | OCH₃ | |
| 42 | H | H | H | H | 4-Cl | — | CH₃ | OCH₃ | |
| 42 | H | H | H | H | 5-CH₃ | — | CH₃ | OCH₃ | |
| 42 | H | H | H | H | H | — | CH₃ | CH₃ | |
| 42 | H | H | H | H | H | — | CH₃ | OCH₃ | |
| 42 | H | H | H | H | H | — | OCH₃ | OCH₃ | |
| 43 | H | H | H | H | H | H | CH₃ | CH₃ | 215–216 |
| 43 | H | H | H | H | H | H | CH₃ | OCH₃ | 206–207 |
| 43 | H | H | H | H | H | H | OCH₃ | OCH₃ | |
| 43 | H | H | H | H | 4-CH₃ | 6-CH₃ | CH₃ | OCH₃ | |
| 43 | H | H | H | H | 3-Cl | 5-CH₃ | CH₃ | OCH₃ | |
| 43 | H | H | H | H | 3-CH₃ | 5-CH₃ | CH₃ | OCH₃ | |
| 43 | H | H | H | H | 4-N(CH₃)₂ | H | CH₃ | OCH₃ | |
| 43 | H | H | H | H | 5-CN | H | CH₃ | OCH₃ | |
| 44 | H | H | H | H | H | H | CH₃ | CH₃ | |
| 44 | H | H | H | H | H | H | CH₃ | OCH₃ | |
| 44 | H | H | H | H | H | H | OCH₃ | OCH₃ | |
| 45 | H | H | H | H | H | H | CH₃ | CH₃ | |
| 45 | H | H | H | H | H | H | CH₃ | OCH₃ | |
| 45 | H | H | H | H | H | H | OCH₃ | OCH₃ | |
| 46 | H | H | H | H | H | H | CH₃ | CH₃ | |
| 46 | H | H | H | H | H | H | CH₃ | OCH₃ | |
| 46 | H | H | H | H | H | H | OCH₃ | OCH₃ | |
| 46 | H | H | H | H | 5-CH₃ | H | CH₃ | OCH₃ | |
| 46 | H | H | H | H | 5-CH₃ | 6-CH₃ | CH₃ | OCH₃ | |

TABLE II-continued

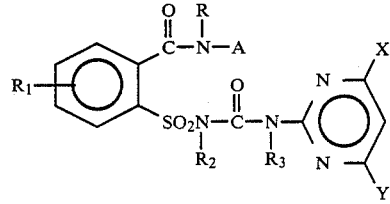

| A | R | $R_1$ | $R_2$ | $R_3$ | $R_5$ | $R_6$ | X | Y | m.p.(°C.) |
|---|---|---|---|---|---|---|---|---|---|
| 47 | H | H | H | H | H | H | $CH_3$ | $CH_3$ | |
| 47 | H | H | H | H | H | H | $CH_3$ | $OCH_3$ | |
| 47 | H | H | H | H | H | H | $OCH_3$ | $OCH_3$ | |
| 47 | H | H | H | H | 6-$CH_3$ | H | $CH_3$ | $OCH_3$ | |
| 47 | H | H | H | H | 3-$CH_3$ | 6-$CH_3$ | $CH_3$ | $OCH_3$ | |
| 48 | H | H | H | H | 5-$CH_3$ | H | $CH_3$ | $OCH_3$ | |
| 48 | H | H | H | H | 5-Cl | H | $CH_3$ | $OCH_3$ | |
| 48 | H | H | H | H | H | H | $CH_3$ | $CH_3$ | |
| 48 | H | H | H | H | H | H | $CH_3$ | $OCH_3$ | |
| 48 | H | H | H | H | H | H | $OCH_3$ | $OCH_3$ | |
| 49 | H | H | H | H | H | H | $CH_3$ | $CH_3$ | |
| 49 | H | H | H | H | H | H | $CH_3$ | $OCH_3$ | |
| 49 | H | H | H | H | 4-$CH_3$ | 6-$CH_3$ | $CH_3$ | $CH_3$ | 190–191 |
| 49 | H | H | H | H | H | H | $OCH_3$ | $OCH_3$ | |
| 49 | H | H | H | H | 4-$CH_3$ | 6-$CH_3$ | $CH_3$ | $OCH_3$ | 184–185 |
| 49 | H | H | H | H | 4-$CH_3$ | 6-$CH_3$ | $OCH_3$ | $OCH_3$ | 198–199 |
| 49 | H | H | H | H | 4-$OCH_3$ | 6-$OCH_3$ | $CH_3$ | $CH_3$ | 188–190 |
| 49 | H | H | H | H | 4-$OCH_3$ | 6-$OCH_3$ | $CH_3$ | $OCH_3$ | 202–204 |
| 49 | H | H | H | H | 4-Cl | 6-Cl | $CH_3$ | $OCH_3$ | |
| 49 | H | H | H | H | 4-Cl | 4-$N(CH_3)_2$ | $CH_3$ | $OCH_3$ | |
| 49 | H | H | H | H | 4-$OCH_3$ | 6-$SCH_3$ | $CH_3$ | $OCH_3$ | |
| 49 | H | H | H | H | 4-Cl | 6-CN | $CH_3$ | $OCH_3$ | |
| 50 | H | H | H | H | H | H | $CH_3$ | $CH_3$ | |
| 50 | H | H | H | H | H | H | $CH_3$ | $OCH_3$ | |
| 50 | H | H | H | H | H | H | $OCH_3$ | $OCH_3$ | |
| 50 | H | H | H | H | 2-$CH_3$ | 6-$CH_3$ | $CH_3$ | $OCH_3$ | |
| 50 | H | H | H | H | 2-$CH_3$ | 6-$OCH_3$ | $CH_3$ | $OCH_3$ | |
| 50 | H | H | H | H | 2-$CH_3$ | 6-Cl | $CH_3$ | $OCH_3$ | |
| 51 | H | H | H | H | H | H | $CH_3$ | $CH_3$ | |
| 51 | H | H | H | H | H | H | $CH_3$ | $OCH_3$ | |
| 51 | H | H | H | H | H | H | $OCH_3$ | $OCH_3$ | |
| 51 | H | H | H | H | 2-$CH_3$ | H | $CH_3$ | $OCH_3$ | |
| 51 | H | H | H | H | 5-$CH_3$ | H | $CH_3$ | $OCH_3$ | |
| 51 | H | H | H | H | $OCH_3$ | H | $CH_3$ | $OCH_3$ | |
| 52 | H | H | H | H | H | H | $CH_3$ | $CH_3$ | |
| 52 | H | H | H | H | H | H | $CH_3$ | $OCH_3$ | |
| 52 | H | H | H | H | H | H | $OCH_3$ | $OCH_3$ | |
| 52 | H | H | H | H | $CH_3$ | $CH_3$ | $CH_3$ | $OCH_3$ | |
| 52 | H | H | H | H | $CH_3$ | $OCH_3$ | $CH_3$ | $OCH_3$ | |
| 52 | H | H | H | H | $OCH_3$ | $OCH_3$ | $CH_3$ | $OCH_3$ | |
| 53 | H | H | H | H | H | H | $CH_3$ | $CH_3$ | |
| 53 | H | H | H | H | H | H | $CH_3$ | $OCH_3$ | |
| 53 | H | H | H | H | H | H | $OCH_3$ | $OCH_3$ | |
| 53 | H | H | H | H | 5-$CH_3$ | 6-$CH_3$ | $OCH_3$ | $OCH_3$ | |
| 54 | H | H | H | H | H | H | $CH_3$ | $CH_3$ | |
| 54 | H | H | H | H | H | H | $CH_3$ | $OCH_3$ | |
| 54 | H | H | H | H | H | H | $OCH_3$ | $OCH_3$ | |
| 55 | H | H | H | H | H | H | $CH_3$ | $CH_3$ | |
| 55 | H | H | H | H | H | H | $CH_3$ | $OCH_3$ | |
| 55 | H | H | H | H | H | H | $OCH_3$ | $OCH_3$ | |
| 56 | H | H | H | H | H | — | $CH_3$ | $CH_3$ | |
| 56 | H | H | H | H | H | — | $CH_3$ | $OCH_3$ | |
| 56 | H | H | H | H | H | — | $OCH_3$ | $OCH_3$ | |
| 56 | H | H | H | H | 6-$CH_3$ | — | $OCH_3$ | $OCH_3$ | |
| 57 | H | H | H | H | H | — | $CH_3$ | $OCH_3$ | |
| 57 | H | H | H | H | 4-$CH_3$ | — | $CH_3$ | $OCH_3$ | |
| 58 | H | H | H | H | H | — | $CH_3$ | $OCH_3$ | |
| 58 | H | H | H | H | 4-$CH_3$ | — | $CH_3$ | $OCH_3$ | |
| 59 | H | H | H | H | H | — | $CH_3$ | $CH_3$ | |
| 59 | H | H | H | H | H | — | $CH_3$ | $OCH_3$ | |
| 59 | H | H | H | H | H | — | $OCH_3$ | $OCH_3$ | |
| 59 | H | H | H | H | 4-$CH_3$ | — | $OCH_3$ | $OCH_3$ | |
| 59 | H | H | H | H | 5-$CH_3$ | — | $OCH_3$ | $OCH_3$ | |
| 60 | H | H | H | H | 4-$CH_3$ | — | $CH_3$ | $OCH_3$ | |
| 61 | H | H | H | H | H | — | $CH_3$ | $OCH_3$ | |
| 61 | H | H | H | H | 5-$CH_3$ | — | $CH_3$ | $OCH_3$ | |
| 62 | H | H | H | H | H | — | $CH_3$ | $OCH_3$ | |
| 62 | H | H | H | H | H | — | $OCH_3$ | $OCH_3$ | |
| 63 | H | H | H | H | H | — | $CH_3$ | $OCH_3$ | |
| 63 | H | H | H | H | H | — | $OCH_3$ | $OCH_3$ | |

TABLE II-continued

| A | R | R₁ | R₂ | R₃ | R₅ | R₆ | X | Y | m.p.(°C.) |
|---|---|----|----|----|----|----|---|---|-----------|
| 64 | H | H | H | H | H | — | CH₃ | OCH₃ | |
| 64 | H | H | H | H | H | — | OCH₃ | OCH₃ | |
| 65 | H | H | H | H | H | — | CH₃ | OCH₃ | |
| 66 | H | H | H | H | H | — | OCH₃ | OCH₃ | |
| 67 | H | H | H | H | H | — | CH₃ | OCH₃ | |
| 67 | H | H | H | H | H | — | OCH₃ | OCH₃ | |
| 68 | H | H | H | H | H | — | CH₃ | OCH₃ | |
| 68 | H | H | H | H | H | — | OCH₃ | OCH₃ | |
| 69 | H | H | H | H | H | — | CH₃ | OCH₃ | |
| 69 | H | H | H | H | H | — | OCH₃ | OCH₃ | |
| 70 | H | H | H | H | H | — | CH₃ | OCH₃ | |
| 70 | H | H | H | H | H | — | OCH₃ | OCH₃ | |
| 71 | H | H | H | H | H | H | CH₃ | CH₃ | |
| 71 | H | H | H | H | H | H | CH₃ | OCH₃ | |
| 71 | H | H | H | H | H | H | OCH₃ | OCH₃ | |
| 71 | H | H | H | H | CH₃ | CH₃ | CH₃ | CH₃ | |
| 71 | H | H | H | H | CH₃ | CH₃ | CH₃ | OCH₃ | |
| 71 | H | H | H | H | CH₃ | CH₃ | OCH₃ | OCH₃ | |
| 71 | H | H | H | H | CH₃ | OCH₃ | OCH₃ | OCH₃ | |
| 71 | H | H | H | H | OCH₃ | OCH₃ | CH₃ | OCH₃ | |
| 72 | H | H | H | H | H | H | CH₃ | CH₃ | |
| 72 | H | H | H | H | H | H | CH₃ | OCH₃ | |
| 72 | H | H | H | H | H | H | OCH₃ | OCH₃ | |
| 72 | H | H | H | H | CH₃ | CH₃ | CH₃ | CH₃ | |
| 72 | H | H | H | H | CH₃ | CH₃ | CH₃ | OCH₃ | |
| 72 | H | H | H | H | CH₃ | CH₃ | OCH₃ | OCH₃ | |
| 72 | H | H | H | H | CH₃ | OCH₃ | CH₃ | OCH₃ | |
| 72 | H | H | H | H | OCH₃ | OCH₃ | CH₃ | OCH₃ | |
| 73 | H | H | H | H | H | H | CH₃ | CH₃ | |
| 73 | H | H | H | H | H | H | CH₃ | OCH₃ | |
| 73 | H | H | H | H | H | H | OCH₃ | OCH₃ | |
| 73 | H | H | H | H | CH₃ | CH₃ | CH₃ | CH₃ | |
| 73 | H | H | H | H | CH₃ | CH₃ | CH₃ | OCH₃ | |
| 73 | H | H | H | H | CH₃ | CH₃ | OCH₃ | OCH₃ | |
| 73 | H | H | H | H | CH₃ | OCH₃ | CH₃ | OCH₃ | |
| 73 | H | H | H | H | OCH₃ | OCH₃ | CH₃ | OCH₃ | |
| 74 | H | H | H | H | CH₃ | CH₃ | CH₃ | CH₃ | |
| 74 | H | H | H | H | CH₃ | CH₃ | CH₃ | OCH₃ | |
| 74 | H | H | H | H | CH₃ | CH₃ | OCH₃ | OCH₃ | |
| 32 | H | H | H | H | H | H | Cl | OCH₃ | |
| 32 | H | H | H | H | H | H | OCH₃ | C₂H₅ | |
| 32 | H | H | H | H | H | H | OCH₃ | OC₂H₅ | |
| 32 | H | H | H | H | H | H | OCH₃ | CH₂OCH₃ | |
| 35 | H | H | H | H | H | — | Cl | CH₃ | |
| 35 | H | H | H | H | H | — | CH₃ | C₂H₅ | |
| 35 | H | H | H | H | H | — | CH₃ | OC₂H₅ | |
| 35 | H | H | H | H | H | — | CH₃ | CH₂OCH₃ | |
| 35 | H | H | H | H | H | — | CH₃ | H | |
| 32 | H | H | H | H | H | — | Cl | NH₂ | |
| 32 | H | H | H | H | H | — | Cl | NHCH₃ | |
| 35 | H | H | H | H | H | — | Cl | N(CH₃)₂ | |

TABLE III

| A | R | R₁ | R₂ | R₃ | R₅ | R₆ | X | Y | m.p. (°C.) |
|---|---|----|----|----|----|----|---|---|------------|
| 1 | H | H | H | H | H | H | CH₃ | CH₃ | |
| 1 | H | H | H | H | 4-CH₃ | H | CH₃ | CH₃ | |
| 2 | H | H | H | H | H | H | CH₃ | OCH₃ | |
| 2 | H | H | H | H | 5-CH₃ | H | CH₃ | CH₃ | |

TABLE III-continued

| A | R | R₁ | R₂ | R₃ | R₅ | R₆ | X | Y | m.p. (°C.) |
|---|---|---|---|---|---|---|---|---|---|
| 3 | H | H | H | H | 2-CH₃ | 5-CH₃ | CH₃ | OCH₃ | |
| 3 | H | H | H | H | H | H | CH₃ | OCH₃ | |
| 4 | H | H | H | H | H | H | OCH₃ | OCH₃ | |
| 5 | H | H | H | H | H | H | CH₃ | OCH₃ | |
| 5 | H | 5-Cl | H | H | H | H | OCH₃ | OCH₃ | |
| 6 | H | H | H | H | H | H | CH₃ | CH₃ | |
| 6 | H | H | H | H | H | H | CH₃ | OCH₃ | 194–197 |
| 7 | H | H | H | H | 3-CH₃ | 4-CH₃ | CH₃ | CH₃ | |
| 8 | H | 5-F | H | H | H | H | OCH₃ | OCH₃ | |
| 8 | H | 5-Br | H | H | 4-CH₃ | H | CH₃ | OCH₃ | |
| 9 | H | H | H | H | H | H | CH₃ | CH₃ | |
| 10 | H | H | H | H | H | H | CH₃ | OCH₃ | |
| 11 | H | H | H | H | H | H | OCH₃ | OCH₃ | |
| 12 | H | H | H | H | 5-SCH₃ | — | CH₃ | CH₃ | |
| 12 | H | H | H | H | 5-CH₃ | — | CH₃ | OCH₃ | |
| 12 | H | H | H | H | H | — | CH₃ | CH₃ | |
| 12 | H | H | H | H | H | — | CH₃ | OCH₃ | 176–179 |
| 13 | H | H | H | H | 3-CH₃ | — | OCH₃ | OCH₃ | |
| 14 | H | H | H | H | 3-CH₃ | — | CH₃ | CH₃ | |
| 15 | H | H | H | H | H | — | CH₃ | CH₃ | |
| 15 | H | H | H | H | CH₃ | — | OCH₃ | OCH₃ | |
| 16 | H | H | H | H | H | — | CH₃ | OCH₃ | |
| 17 | H | 5-F | H | H | — | — | CH₃ | CH₃ | |
| 18 | H | H | H | H | CH₃ | — | OCH₃ | OCH₃ | |
| 19 | H | H | H | H | CH₃ | CH₃ | CH₃ | CH₃ | |
| 19 | H | H | H | H | CH₃ | CH₃ | CH₃ | OCH₃ | 142–144 |
| 20 | H | H | H | H | H | H | CH₃ | CH₃ | |
| 21 | H | 5-OCH₃ | H | H | H | H | OCH₃ | OCH₃ | |
| 22 | H | 5-CF₃ | H | H | H | H | CH₃ | CH₃ | |
| 22 | H | 5-NO₂ | H | H | H | — | CH₃ | OCH₃ | |
| 23 | H | H | H | H | H | — | OCH₃ | OCH₃ | |
| 24 | H | H | H | H | 5-CH₃ | — | CH₃ | CH₃ | |
| 25 | H | H | H | H | H | — | CH₃ | CH₃ | |
| 25 | H | H | H | H | CH₃ | — | CH₃ | OCH₃ | |
| 26 | H | H | H | H | H | — | CH₃ | CH₃ | |
| 27 | H | 5-NO₂ | H | H | H | — | OCH₃ | OCH₃ | |
| 28 | H | H | H | H | H | — | CH₃ | CH₃ | |
| 29 | H | H | H | H | H | — | CH₃ | OCH₃ | |
| 29 | H | H | H | H | H | — | OCH₃ | OCH₃ | |
| 30 | H | H | H | H | H | — | CH₃ | CH₃ | |
| 31 | H | 5-Cl | H | H | H | — | CH₃ | CH₃ | |
| 31 | H | H | H | H | H | — | CH₃ | OCH₃ | |
| 31 | H | H | H | H | H | — | OCH₃ | OCH₃ | |
| 32 | H | H | H | H | H | H | CH₃ | CH₃ | |
| 32 | H | H | H | H | H | H | CH₃ | OCH₃ | |
| 32 | H | H | H | H | 4-CH₃ | H | OCH₃ | OCH₃ | |
| 32 | H | H | H | H | H | H | OCH₃ | OCH₃ | |
| 33 | H | H | H | H | H | — | CH₃ | CH₃ | |
| 33 | H | H | H | H | H | — | CH₃ | OCH₃ | |
| 33 | H | H | H | H | 2-CH₃ | — | OCH₃ | OCH₃ | |
| 34 | H | H | H | H | 2-CH₃ | — | CH₃ | CH₃ | |
| 34 | H | H | H | H | H | — | OCH₃ | OCH₃ | |
| 34 | H | H | H | H | H | — | CH₃ | CH₃ | |
| 35 | H | H | H | H | H | — | CH₃ | CH₃ | |
| 35 | H | H | H | H | 5-CH₃ | — | CH₃ | OCH₃ | |
| 35 | H | H | H | H | H | — | CH₃ | OCH₃ | |
| 35 | CH₃ | H | H | H | H | — | OCH₃ | OCH₃ | |
| 35 | H | H | CH₃ | H | H | — | OCH₃ | OCH₃ | |
| 35 | H | H | H | CH₃ | H | — | OCH₃ | OCH₃ | |
| 36 | H | H | H | H | H | — | CH₃ | CH₃ | |
| 36 | H | H | H | H | H | — | CH₃ | OCH₃ | |
| 36 | H | H | H | H | H | — | OCH₃ | OCH₃ | |
| 37 | H | H | H | H | H | — | CH₃ | CH₃ | |
| 37 | H | H | H | H | H | — | CH₃ | OCH₃ | |
| 37 | H | H | H | H | H | — | OCH₃ | OCH₃ | |
| 38 | H | H | H | H | H | — | OCH₃ | OCH₃ | |
| 38 | H | H | H | H | CH₃ | — | CH₃ | OCH₃ | |
| 39 | H | H | H | H | H | — | CH₃ | CH₃ | |
| 39 | H | H | H | H | H | — | CH₃ | OCH₃ | |
| 40 | H | H | H | H | H | — | CH₃ | CH₃ | |

TABLE III-continued

| A | R | R₁ | R₂ | R₃ | R₅ | R₆ | X | Y | m.p. (°C.) |
|---|---|---|---|---|---|---|---|---|---|
| 40 | H | H | H | H | H | — | CH₃ | OCH₃ | |
| 41 | H | H | H | H | 4-Cl | — | CH₃ | CH₃ | |
| 41 | H | H | H | H | 4-CN | — | OCH₃ | CH₃ | |
| 41 | H | H | H | H | H | — | CH₃ | CH₃ | |
| 41 | H | H | H | H | H | — | CH₃ | OCH₃ | |
| 41 | H | H | H | H | H | — | OCH₃ | OCH₃ | |
| 42 | H | H | H | H | 4-Cl | — | CH₃ | OCH₃ | |
| 42 | H | H | H | H | 5-CH₃ | — | CH₃ | OCH₃ | |
| 42 | H | H | H | H | H | — | CH₃ | CH₃ | |
| 42 | H | H | H | H | H | — | CH₃ | OCH₃ | |
| 42 | H | H | H | H | H | — | OCH₃ | OCH₃ | |
| 43 | H | H | H | H | H | H | CH₃ | CH₃ | |
| 43 | H | H | H | H | H | H | CH₃ | OCH₃ | 161–163 |
| 43 | H | H | H | H | H | H | OCH₃ | OCH₃ | |
| 43 | H | H | H | H | 4-CH₃ | 6-CH₃ | CH₃ | OCH₃ | |
| 43 | H | H | H | H | 3-Cl | 5-CH₃ | CH₃ | OCH₃ | |
| 43 | H | H | H | H | 3-CH₃ | 5-CH₃ | CH₃ | OCH₃ | |
| 43 | H | H | H | H | 4-N(CH₃)₂ | H | CH₃ | OCH₃ | |
| 43 | H | H | H | H | 5-CN | H | CH₃ | OCH₃ | |
| 44 | H | H | H | H | H | H | CH₃ | CH₃ | |
| 44 | H | H | H | H | H | H | CH₃ | OCH₃ | |
| 44 | H | H | H | H | H | H | OCH₃ | OCH₃ | |
| 45 | H | H | H | H | H | H | CH₃ | CH₃ | |
| 45 | H | H | H | H | H | H | CH₃ | OCH₃ | |
| 45 | H | H | H | H | H | H | OCH₃ | OCH₃ | |
| 46 | H | H | H | H | H | H | CH₃ | CH₃ | |
| 46 | H | H | H | H | H | H | CH₃ | OCH₃ | |
| 46 | H | H | H | H | H | H | OCH₃ | OCH₃ | |
| 46 | H | H | H | H | 5-CH₃ | H | CH₃ | OCH₃ | |
| 46 | H | H | H | H | 5-CH₃ | 6-CH₃ | CH₃ | OCH₃ | |
| 47 | H | H | H | H | H | H | CH₃ | CH₃ | |
| 47 | H | H | H | H | H | H | CH₃ | OCH₃ | |
| 47 | H | H | H | H | H | H | OCH₃ | OCH₃ | |
| 47 | H | H | H | H | 6-CH₃ | H | CH₃ | OCH₃ | |
| 47 | H | H | H | H | 3-CH₃ | 6-CH₃ | CH₃ | OCH₃ | |
| 48 | H | H | H | H | 5-CH₃ | H | CH₃ | OCH₃ | |
| 48 | H | H | H | H | 5-Cl | H | CH₃ | OCH₃ | |
| 48 | H | H | H | H | H | H | CH₃ | CH₃ | |
| 48 | H | H | H | H | H | H | CH₃ | OCH₃ | |
| 48 | H | H | H | H | H | H | OCH₃ | OCH₃ | |
| 49 | H | H | H | H | H | H | CH₃ | CH₃ | |
| 49 | H | H | H | H | H | H | CH₃ | OCH₃ | |
| 49 | H | H | H | H | 4-CH₃ | 6-CH₃ | CH₃ | CH₃ | |
| 49 | H | H | H | H | H | H | OCH₃ | OCH₃ | |
| 49 | H | H | H | H | 4-CH₃ | 6-CH₃ | CH₃ | OCH₃ | 172–173 |
| 49 | H | H | H | H | 4-CH₃ | 6-CH₃ | OCH₃ | OCH₃ | |
| 49 | H | H | H | H | 4-OCH₃ | 6-OCH₃ | CH₃ | CH₃ | |
| 49 | H | H | H | H | 4-OCH₃ | 6-OCH₃ | CH₃ | OCH₃ | 194–196 |
| 49 | H | H | H | H | 4-Cl | 6-Cl | CH₃ | OCH₃ | |
| 49 | H | H | H | H | 4-Cl | 4-N(CH₃)₂ | CH₃ | OCH₃ | |
| 49 | H | H | H | H | 4-OCH₃ | 6-SCH₃ | CH₃ | OCH₃ | |
| 49 | H | H | H | H | 4-Cl | 6-CN | CH₃ | OCH₃ | |
| 50 | H | H | H | H | H | H | CH₃ | CH₃ | |
| 50 | H | H | H | H | H | H | CH₃ | OCH₃ | |
| 50 | H | H | H | H | H | H | OCH₃ | OCH₃ | |
| 50 | H | H | H | H | 2-CH₃ | 6-CH₃ | CH₃ | OCH₃ | |
| 50 | H | H | H | H | 2-CH₃ | 6-OCH₃ | CH₃ | OCH₃ | |
| 50 | H | H | H | H | 2-CH₃ | 6-Cl | CH₃ | OCH₃ | |
| 51 | H | H | H | H | H | H | CH₃ | CH₃ | |
| 51 | H | H | H | H | H | H | CH₃ | OCH₃ | |
| 51 | H | H | H | H | H | H | OCH₃ | OCH₃ | |
| 51 | H | H | H | H | 2-CH₃ | H | CH₃ | OCH₃ | |
| 51 | H | H | H | H | 5-CH₃ | H | CH₃ | OCH₃ | |
| 51 | H | H | H | H | OCH₃ | H | CH₃ | OCH₃ | |
| 52 | H | H | H | H | H | H | CH₃ | CH₃ | |
| 52 | H | H | H | H | H | H | CH₃ | OCH₃ | |
| 52 | H | H | H | H | H | H | OCH₃ | OCH₃ | |
| 52 | H | H | H | H | CH₃ | CH₃ | CH₃ | OCH₃ | |
| 52 | H | H | H | H | CH₃ | OCH₃ | CH₃ | OCH₃ | |
| 52 | H | H | H | H | OCH₃ | OCH₃ | CH₃ | OCH₃ | |
| 53 | H | H | H | H | H | H | CH₃ | CH₃ | |

TABLE III-continued

| A | R | R₁ | R₂ | R₃ | R₅ | R₆ | X | Y | m.p. (°C.) |
|---|---|----|----|----|----|----|----|----|-----------|
| 53 | H | H | H | H | H | H | CH₃ | OCH₃ | |
| 53 | H | H | H | H | H | H | OCH₃ | OCH₃ | |
| 53 | H | H | H | H | 5-CH₃ | 6-CH₃ | OCH₃ | OCH₃ | |
| 54 | H | H | H | H | H | H | CH₃ | CH₃ | |
| 54 | H | H | H | H | H | H | CH₃ | OCH₃ | |
| 54 | H | H | H | H | H | H | OCH₃ | OCH₃ | |
| 55 | H | H | H | H | H | H | CH₃ | CH₃ | |
| 55 | H | H | H | H | H | H | CH₃ | OCH₃ | |
| 55 | H | H | H | H | H | H | OCH₃ | OCH₃ | |
| 56 | H | H | H | H | H | — | CH₃ | CH₃ | |
| 56 | H | H | H | H | H | — | CH₃ | OCH₃ | |
| 56 | H | H | H | H | H | — | OCH₃ | OCH₃ | |
| 56 | H | H | H | H | 6-CH₃ | — | OCH₃ | OCH₃ | |
| 57 | H | H | H | H | H | — | CH₃ | OCH₃ | |
| 57 | H | H | H | H | 4-CH₃ | — | CH₃ | OCH₃ | |
| 58 | H | H | H | H | H | — | CH₃ | OCH₃ | |
| 58 | H | H | H | H | 4-CH₃ | — | CH₃ | OCH₃ | |
| 59 | H | H | H | H | H | — | CH₃ | CH₃ | |
| 59 | H | H | H | H | H | — | CH₃ | OCH₃ | |
| 59 | H | H | H | H | H | — | OCH₃ | OCH₃ | |
| 59 | H | H | H | H | 4-CH₃ | — | OCH₃ | OCH₃ | |
| 59 | H | H | H | H | 5-CH₃ | — | OCH₃ | OCH₃ | |
| 60 | H | H | H | H | 4-CH₃ | — | CH₃ | OCH₃ | |
| 61 | H | H | H | H | H | — | CH₃ | OCH₃ | |
| 61 | H | H | H | H | 5-CH₃ | — | CH₃ | OCH₃ | |
| 62 | H | H | H | H | H | — | CH₃ | OCH₃ | |
| 62 | H | H | H | H | H | — | OCH₃ | OCH₃ | |
| 63 | H | H | H | H | H | — | CH₃ | OCH₃ | |
| 63 | H | H | H | H | H | — | OCH₃ | OCH₃ | |
| 64 | H | H | H | H | H | — | CH₃ | OCH₃ | |
| 64 | H | H | H | H | H | — | OCH₃ | OCH₃ | |
| 65 | H | H | H | H | H | — | CH₃ | OCH₃ | |
| 66 | H | H | H | H | H | — | OCH₃ | OCH₃ | |
| 67 | H | H | H | H | H | — | CH₃ | OCH₃ | |
| 67 | H | H | H | H | H | — | OCH₃ | OCH₃ | |
| 68 | H | H | H | H | H | — | CH₃ | OCH₃ | |
| 68 | H | H | H | H | H | — | OCH₃ | OCH₃ | |
| 69 | H | H | H | H | H | — | CH₃ | OCH₃ | |
| 69 | H | H | H | H | H | — | OCH₃ | OCH₃ | |
| 70 | H | H | H | H | H | — | CH₃ | OCH₃ | |
| 70 | H | H | H | H | H | — | OCH₃ | OCH₃ | |
| 71 | H | H | H | H | H | H | CH₃ | CH₃ | |
| 71 | H | H | H | H | H | H | CH₃ | OCH₃ | |
| 71 | H | H | H | H | H | H | OCH₃ | OCH₃ | |
| 71 | H | H | H | H | CH₃ | CH₃ | CH₃ | CH₃ | |
| 71 | H | H | H | H | CH₃ | CH₃ | CH₃ | OCH₃ | |
| 71 | H | H | H | H | CH₃ | CH₃ | OCH₃ | OCH₃ | |
| 71 | H | H | H | H | CH₃ | OCH₃ | OCH₃ | OCH₃ | |
| 71 | H | H | H | H | OCH₃ | OCH₃ | CH₃ | OCH₃ | |
| 72 | H | H | H | H | H | H | CH₃ | CH₃ | |
| 72 | H | H | H | H | H | H | CH₃ | OCH₃ | |
| 72 | H | H | H | H | H | H | OCH₃ | OCH₃ | |
| 72 | H | H | H | H | CH₃ | CH₃ | CH₃ | CH₃ | |
| 72 | H | H | H | H | CH₃ | CH₃ | CH₃ | OCH₃ | |
| 72 | H | H | H | H | CH₃ | CH₃ | OCH₃ | OCH₃ | |
| 72 | H | H | H | H | CH₃ | OCH₃ | OCH₃ | OCH₃ | |
| 72 | H | H | H | H | OCH₃ | OCH₃ | CH₃ | OCH₃ | |
| 73 | H | H | H | H | H | H | CH₃ | CH₃ | |
| 73 | H | H | H | H | H | H | CH₃ | OCH₃ | |
| 73 | H | H | H | H | H | H | OCH₃ | OCH₃ | |
| 73 | H | H | H | H | CH₃ | CH₃ | CH₃ | CH₃ | |
| 73 | H | H | H | H | CH₃ | CH₃ | CH₃ | OCH₃ | |
| 73 | H | H | H | H | CH₃ | CH₃ | OCH₃ | OCH₃ | |
| 73 | H | H | H | H | CH₃ | OCH₃ | OCH₃ | OCH₃ | |
| 73 | H | H | H | H | OCH₃ | OCH₃ | CH₃ | OCH₃ | |
| 74 | H | H | H | H | CH₃ | CH₃ | CH₃ | CH₃ | |
| 74 | H | H | H | H | CH₃ | CH₃ | CH₃ | OCH₃ | |
| 74 | H | H | H | H | CH₃ | CH₃ | OCH₃ | OCH₃ | |
| 32 | H | H | H | H | H | H | OCH₃ | C₂H₅ | |
| 32 | H | H | H | H | H | H | OCH₃ | OC₂H₅ | |
| 32 | H | H | H | H | H | H | OCH₃ | CH₂OCH₃ | |

TABLE III-continued $$\underset{R_1}{\underset{\text{SO}_2\text{N}-\text{C}-\text{N}}{\text{C}-\text{N}-\text{A}}}\overset{\text{O R}}{\underset{R_2}{\parallel}}\underset{R_3}{\overset{\text{O}}{\underset{\parallel}{\text{N}}}}\underset{\text{N}}{\overset{\text{X}}{\underset{\text{Y}}{\bigvee}}}$$

| A | R | R₁ | R₂ | R₃ | R₅ | R₆ | X | Y | m.p. (°C.) |
|---|---|----|----|----|----|----|----|----|----|
| 35 | H | H | H | H | H | — | CH₃ | C₂H₅ | |
| 35 | H | H | H | H | H | — | CH₃ | OC₂H₅ | |
| 35 | H | H | H | H | H | — | CH₃ | CH₂OCH₃ | |
| 35 | H | H | H | H | H | — | CH₃ | H | |

TABLE IV

| A | R | R₁ | R₂ | R₃ | R₅ | R₆ | X | Y | m.p. (°C.) |
|---|---|----|----|----|----|----|----|----|----|
| 1 | H | H | H | H | H | H | CH₃ | CH₃ | |
| 1 | H | H | H | H | 4-CH₃ | H | CH₃ | CH₃ | |
| 2 | H | H | H | H | H | H | CH₃ | OCH₃ | |
| 2 | H | H | H | H | 5-CH₃ | H | CH₃ | CH₃ | |
| 3 | H | H | H | H | 2-CH₃ | 5-CH₃ | CH₃ | OCH₃ | |
| 3 | H | H | H | H | H | H | CH₃ | OCH₃ | |
| 4 | H | H | H | H | H | H | CH₃ | CH₃ | |
| 5 | H | H | H | H | H | H | CH₃ | OCH₃ | |
| 5 | H | 5-Cl | H | H | H | H | CH₃ | H | |
| 6 | H | H | H | H | H | H | CH₃ | CH₃ | |
| 6 | H | H | H | H | H | H | CH₃ | OCH₃ | |
| 7 | H | H | H | H | 3-CH₃ | 4-CH₃ | CH₃ | CH₃ | |
| 8 | H | 5-F | H | H | H | H | CH₃ | CH₃ | |
| 8 | H | 5-Br | H | H | 4-CH₃ | H | CH₃ | OCH₃ | |
| 9 | H | H | H | H | H | H | CH₃ | CH₃ | |
| 10 | H | H | H | H | H | H | CH₃ | OCH₃ | |
| 11 | H | H | H | H | H | H | CH₃ | CH₃ | |
| 12 | H | H | H | H | 5-SCH₃ | — | CH₃ | CH₃ | |
| 12 | H | H | H | H | 5-CH₃ | — | CH₃ | H | |
| 12 | H | H | H | H | H | — | CH₃ | CH₃ | |
| 12 | H | H | H | H | H | — | CH₃ | OCH₃ | |
| 13 | H | H | H | H | 3-CH₃ | — | CH₃ | H | |
| 14 | H | H | H | H | 3-CH₃ | — | CH₃ | CH₃ | |
| 15 | H | H | H | H | H | — | CH₃ | CH₃ | |
| 15 | H | H | H | H | CH₃ | — | CH₃ | OCH₃ | |
| 16 | H | H | H | H | H | — | CH₃ | OCH₃ | |
| 17 | H | 5-F | H | H | — | — | CH₃ | CH₃ | |
| 18 | H | H | H | H | CH₃ | — | OCH₃ | CH₃ | |
| 19 | H | H | H | H | CH₃ | CH₃ | CH₃ | CH₃ | |
| 19 | H | H | H | H | CH₃ | CH₃ | CH₃ | OCH₃ | |
| 20 | H | H | H | H | H | H | CH₃ | CH₃ | |
| 21 | H | 5-OCH₃ | H | H | H | H | CH₃ | OCH₃ | |
| 22 | H | 5-CF₃ | H | H | H | H | CH₃ | CH₃ | |
| 22 | H | 5-NO₂ | H | H | H | — | CH₃ | OCH₃ | |
| 23 | H | H | H | H | H | — | CH₃ | H | |
| 24 | H | H | H | H | 5-CH₃ | — | CH₃ | CH₃ | |
| 25 | H | H | H | H | H | — | CH₃ | CH₃ | |
| 25 | H | H | H | H | CH₃ | — | CH₃ | OCH₃ | |
| 26 | H | H | H | H | H | — | CH₃ | CH₃ | |
| 27 | H | 5-NO₂ | H | H | H | — | OCH₃ | CH₃ | |
| 28 | H | H | H | H | H | — | CH₃ | OCH₃ | |
| 29 | H | H | H | H | H | — | CH₃ | CH₃ | |
| 29 | H | H | H | H | H | — | CH₃ | OCH₃ | |
| 29 | H | H | H | H | H | — | OCH₃ | OCH₃ | |
| 30 | H | H | H | H | H | — | CH₃ | CH₃ | |
| 31 | H | 5-Cl | H | H | H | — | CH₃ | CH₃ | |
| 31 | H | H | H | H | H | — | CH₃ | OCH₃ | |
| 31 | H | H | H | H | H | — | OCH₃ | OCH₃ | |
| 32 | H | H | H | H | H | H | CH₃ | CH₃ | |
| 32 | H | H | H | H | H | H | CH₃ | OCH₃ | |
| 32 | H | H | H | H | 4-CH₃ | H | CH₃ | H | |

TABLE IV-continued

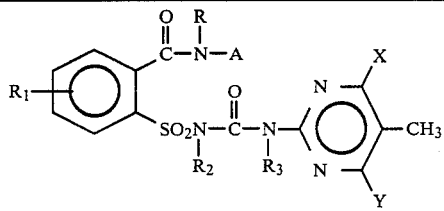

| A | R | R₁ | R₂ | R₃ | R₅ | R₆ | X | Y | m.p. (°C.) |
|---|---|---|---|---|---|---|---|---|---|
| 32 | H | H | H | H | H | H | CH₃ | H | |
| 33 | H | H | H | H | H | — | CH₃ | CH₃ | |
| 33 | H | H | H | H | H | — | CH₃ | OCH₃ | |
| 33 | H | H | H | H | 2-CH₃ | — | OCH₃ | OCH₃ | |
| 34 | H | H | H | H | 2-CH₃ | — | CH₃ | OCH₃ | |
| 34 | H | H | H | H | H | — | CH₃ | H | |
| 34 | H | H | H | H | H | — | CH₃ | CH₃ | |
| 35 | H | H | H | H | H | — | CH₃ | CH₃ | |
| 35 | H | H | H | H | 5-CH₃ | — | CH₃ | OCH₃ | |
| 35 | H | H | H | H | H | — | CH₃ | OCH₃ | |
| 35 | CH₃ | H | H | H | H | — | CH₃ | H | |
| 35 | H | H | CH₃ | H | H | — | CH₃ | CH₃ | |
| 35 | H | H | H | CH₃ | H | — | CH₃ | CH₃ | |
| 36 | H | H | H | H | H | — | CH₃ | CH₃ | |
| 36 | H | H | H | H | H | — | CH₃ | OCH₃ | |
| 36 | H | H | H | H | H | — | OCH₃ | OCH₃ | |
| 37 | H | H | H | H | H | — | CH₃ | CH₃ | |
| 37 | H | H | H | H | H | — | CH₃ | OCH₃ | |
| 37 | H | H | H | H | H | — | OCH₃ | OCH₃ | |
| 38 | H | H | H | H | H | — | OCH₃ | OCH₃ | |
| 38 | H | H | H | H | CH₃ | — | CH₃ | OCH₃ | |
| 39 | H | H | H | H | H | — | CH₃ | CH₃ | |
| 39 | H | H | H | H | H | — | CH₃ | OCH₃ | |
| 40 | H | H | H | H | H | — | CH₃ | CH₃ | |
| 40 | H | H | H | H | H | — | CH₃ | OCH₃ | |
| 41 | H | H | H | H | 4-Cl | — | CH₃ | CH₃ | |
| 41 | H | H | H | H | 4-CN | — | OCH₃ | CH₃ | |
| 41 | H | H | H | H | H | — | OCH₃ | OCH₃ | |
| 41 | H | H | H | H | H | — | CH₃ | CH₃ | |
| 41 | H | H | H | H | H | — | CH₃ | OCH₃ | |
| 41 | H | H | H | H | H | — | CH₃ | H | |
| 42 | H | H | H | H | 4-Cl | — | CH₃ | OCH₃ | |
| 42 | H | H | H | H | 5-CH₃ | — | CH₃ | OCH₃ | |
| 42 | H | H | H | H | H | — | CH₃ | CH₃ | |
| 42 | H | H | H | H | H | — | CH₃ | OCH₃ | |
| 42 | H | H | H | H | H | — | OCH₃ | OCH₃ | |
| 43 | H | H | H | H | H | H | CH₃ | CH₃ | |
| 43 | H | H | H | H | H | H | CH₃ | OCH₃ | |
| 43 | H | H | H | H | H | H | CH₃ | H | |
| 43 | H | H | H | H | 4-CH₃ | 6-CH₃ | CH₃ | CH₃ | |
| 43 | H | H | H | H | 3-Cl | 5-CH₃ | CH₃ | CH₃ | |
| 43 | H | H | H | H | 3-CH₃ | 5-CH₃ | CH₃ | CH₃ | |
| 43 | H | H | H | H | 4-N(CH₃)₂ | H | CH₃ | CH₃ | |
| 43 | H | H | H | H | 5-CN | H | CH₃ | CH₃ | |
| 44 | H | H | H | H | H | H | CH₃ | CH₃ | |
| 44 | H | H | H | H | H | H | CH₃ | OCH₃ | |
| 44 | H | H | H | H | H | H | OCH₃ | OCH₃ | |
| 45 | H | H | H | H | H | H | CH₃ | CH₃ | |
| 45 | H | H | H | H | H | H | CH₃ | OCH₃ | |
| 45 | H | H | H | H | H | H | OCH₃ | OCH₃ | |
| 46 | H | H | H | H | H | H | CH₃ | CH₃ | |
| 46 | H | H | H | H | H | H | CH₃ | OCH₃ | |
| 46 | H | H | H | H | H | H | OCH₃ | OCH₃ | |
| 46 | H | H | H | H | 5-CH₃ | H | CH₃ | CH₃ | |
| 46 | H | H | H | H | 5-CH₃ | 6-CH₃ | CH₃ | H | |
| 47 | H | H | H | H | H | H | CH₃ | CH₃ | |
| 47 | H | H | H | H | H | H | CH₃ | OCH₃ | |
| 47 | H | H | H | H | H | H | OCH₃ | OCH₃ | |
| 47 | H | H | H | H | 6-CH₃ | H | CH₃ | OCH₃ | |
| 47 | H | H | H | H | 3-CH₃ | 6-CH₃ | CH₃ | H | |
| 48 | H | H | H | H | 5-CH₃ | H | CH₃ | CH₃ | |
| 48 | H | H | H | H | 5-Cl | H | CH₃ | OCH₃ | |
| 48 | H | H | H | H | H | H | CH₃ | CH₃ | |
| 48 | H | H | H | H | H | H | CH₃ | OCH₃ | |
| 48 | H | H | H | H | H | H | CH₃ | H | |
| 49 | H | H | H | H | H | H | CH₃ | CH₃ | |
| 49 | H | H | H | H | H | H | CH₃ | OCH₃ | |
| 49 | H | H | H | H | 4-CH₃ | 6-CH₃ | CH₃ | CH₃ | |
| 49 | H | H | H | H | H | H | OCH₃ | OCH₃ | |
| 49 | H | H | H | H | 4-CH₃ | 6-CH₃ | CH₃ | OCH₃ | |

TABLE IV-continued

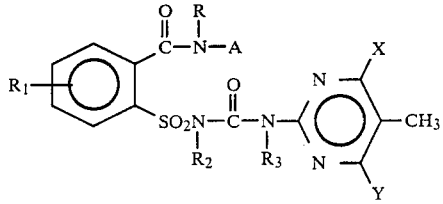

| A | R | R₁ | R₂ | R₃ | R₅ | R₆ | X | Y | m.p. (°C.) |
|---|---|---|---|---|---|---|---|---|---|
| 49 | H | H | H | H | 4-CH₃ | 6-CH₃ | CH₃ | H | |
| 49 | H | H | H | H | 4-OCH₃ | 6-OCH₃ | CH₃ | CH₃ | |
| 49 | H | H | H | H | 4-OCH₃ | 6-OCH₃ | CH₃ | OCH₃ | |
| 49 | H | H | H | H | 4-Cl | 6-Cl | CH₃ | H | |
| 49 | H | H | H | H | 4-Cl | 4-N(CH₃)₂ | CH₃ | H | |
| 49 | H | H | H | H | 4-OCH₃ | 6-SCH₃ | CH₃ | CH₃ | |
| 49 | H | H | H | H | 4-Cl | 6-CN | CH₃ | CH₃ | |
| 50 | H | H | H | H | H | H | CH₃ | CH₃ | |
| 50 | H | H | H | H | H | H | CH₃ | OCH₃ | |
| 50 | H | H | H | H | H | H | OCH₃ | OCH₃ | |
| 50 | H | H | H | H | 2-CH₃ | 6-CH₃ | CH₃ | CH₃ | |
| 50 | H | H | H | H | 2-CH₃ | 6-OCH₃ | CH₃ | CH₃ | |
| 50 | H | H | H | H | 2-CH₃ | 6-Cl | CH₃ | OCH₃ | |
| 51 | H | H | H | H | H | H | CH₃ | CH₃ | |
| 51 | H | H | H | H | H | H | CH₃ | OCH₃ | |
| 51 | H | H | H | H | H | H | OCH₃ | OCH₃ | |
| 51 | H | H | H | H | 2-CH₃ | H | CH₃ | OCH₃ | |
| 51 | H | H | H | H | 5-CH₃ | H | CH₃ | H | |
| 51 | H | H | H | H | OCH₃ | H | CH₃ | OCH₃ | |
| 52 | H | H | H | H | H | H | CH₃ | CH₃ | |
| 52 | H | H | H | H | H | H | CH₃ | OCH₃ | |
| 52 | H | H | H | H | H | H | OCH₃ | OCH₃ | |
| 52 | H | H | H | H | CH₃ | CH₃ | CH₃ | H | |
| 52 | H | H | H | H | CH₃ | OCH₃ | CH₃ | CH₃ | |
| 52 | H | H | H | H | OCH₃ | OCH₃ | CH₃ | CH₃ | |
| 53 | H | H | H | H | H | H | CH₃ | CH₃ | |
| 53 | H | H | H | H | H | H | CH₃ | OCH₃ | |
| 53 | H | H | H | H | H | H | CH₃ | H | |
| 53 | H | H | H | H | 5-CH₃ | 6-CH₃ | CH₃ | CH₃ | |
| 54 | H | H | H | H | H | H | CH₃ | CH₃ | |
| 54 | H | H | H | H | H | H | CH₃ | OCH₃ | |
| 54 | H | H | H | H | H | H | CH₃ | H | |
| 55 | H | H | H | H | H | H | CH₃ | CH₃ | |
| 55 | H | H | H | H | H | H | CH₃ | OCH₃ | |
| 55 | H | H | H | H | H | H | CH₃ | H | |
| 56 | H | H | H | H | H | — | CH₃ | CH₃ | |
| 56 | H | H | H | H | H | — | CH₃ | OCH₃ | |
| 56 | H | H | H | H | H | — | OCH₃ | OCH₃ | |
| 56 | H | H | H | H | 6-CH₃ | — | CH₃ | CH₃ | |
| 57 | H | H | H | H | H | — | CH₃ | OCH₃ | |
| 57 | H | H | H | H | 4-CH₃ | — | CH₃ | CH₃ | |
| 58 | H | H | H | H | H | — | CH₃ | OCH₃ | |
| 58 | H | H | H | H | 4-CH₃ | — | CH₃ | CH₃ | |
| 59 | H | H | H | H | H | — | CH₃ | CH₃ | |
| 59 | H | H | H | H | H | — | CH₃ | OCH₃ | |
| 59 | H | H | H | H | H | — | OCH₃ | OCH₃ | |
| 59 | H | H | H | H | 4-CH₃ | — | CH₃ | CH₃ | |
| 59 | H | H | H | H | 5-CH₃ | — | CH₃ | H | |
| 60 | H | H | H | H | 4-CH₃ | — | CH₃ | CH₃ | |
| 61 | H | H | H | H | H | — | CH₃ | OCH₃ | |
| 61 | H | H | H | H | 5-CH₃ | — | CH₃ | CH₃ | |
| 62 | H | H | H | H | H | — | CH₃ | OCH₃ | |
| 62 | H | H | H | H | H | — | OCH₃ | OCH₃ | |
| 63 | H | H | H | H | H | — | CH₃ | OCH₃ | |
| 63 | H | H | H | H | H | — | CH₃ | CH₃ | |
| 64 | H | H | H | H | H | — | CH₃ | OCH₃ | |
| 64 | H | H | H | H | H | — | CH₃ | CH₃ | |
| 65 | H | H | H | H | H | — | CH₃ | OCH₃ | |
| 66 | H | H | H | H | H | — | CH₃ | CH₃ | |
| 67 | H | H | H | H | H | — | CH₃ | OCH₃ | |
| 67 | H | H | H | H | H | — | CH₃ | CH₃ | |
| 68 | H | H | H | H | H | — | CH₃ | OCH₃ | |
| 68 | H | H | H | H | H | — | CH₃ | CH₃ | |
| 69 | H | H | H | H | H | — | CH₃ | OCH₃ | |
| 69 | H | H | H | H | H | — | CH₃ | CH₃ | |
| 70 | H | H | H | H | H | — | CH₃ | OCH₃ | |
| 70 | H | H | H | H | H | — | CH₃ | CH₃ | |
| 71 | H | H | H | H | H | H | CH₃ | CH₃ | |
| 71 | H | H | H | H | H | H | CH₃ | OCH₃ | |
| 71 | H | H | H | H | H | H | OCH₃ | OCH₃ | |

TABLE IV-continued

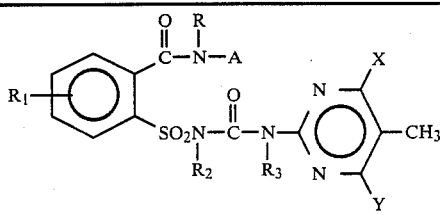

| A | R | R₁ | R₂ | R₃ | R₅ | R₆ | X | Y | m.p. (°C.) |
|---|---|----|----|----|----|----|---|---|------------|
| 71 | H | H | H | H | CH₃ | CH₃ | CH₃ | CH₃ | |
| 71 | H | H | H | H | CH₃ | CH₃ | CH₃ | OCH₃ | |
| 71 | H | H | H | H | CH₃ | CH₃ | CH₃ | H | |
| 71 | H | H | H | H | CH₃ | OCH₃ | CH₃ | CH₃ | |
| 71 | H | H | H | H | OCH₃ | OCH₃ | CH₃ | CH₃ | |
| 72 | H | H | H | H | H | H | CH₃ | CH₃ | |
| 72 | H | H | H | H | H | H | CH₃ | OCH₃ | |
| 72 | H | H | H | H | H | H | OCH₃ | OCH₃ | |
| 72 | H | H | H | H | CH₃ | CH₃ | CH₃ | CH₃ | |
| 72 | H | H | H | H | CH₃ | CH₃ | CH₃ | OCH₃ | |
| 72 | H | H | H | H | CH₃ | CH₃ | CH₃ | H | |
| 72 | H | H | H | H | CH₃ | OCH₃ | CH₃ | CH₃ | |
| 72 | H | H | H | H | OCH₃ | OCH₃ | CH₃ | CH₃ | |
| 73 | H | H | H | H | H | H | CH₃ | CH₃ | |
| 73 | H | H | H | H | H | H | CH₃ | OCH₃ | |
| 73 | H | H | H | H | H | H | OCH₃ | OCH₃ | |
| 73 | H | H | H | H | CH₃ | CH₃ | CH₃ | CH₃ | |
| 73 | H | H | H | H | CH₃ | CH₃ | CH₃ | OCH₃ | |
| 73 | H | H | H | H | CH₃ | CH₃ | CH₃ | H | |
| 73 | H | H | H | H | CH₃ | OCH₃ | CH₃ | CH₃ | |
| 73 | H | H | H | H | OCH₃ | OCH₃ | CH₃ | CH₃ | |
| 74 | H | H | H | H | CH₃ | CH₃ | CH₃ | CH₃ | |
| 74 | H | H | H | H | CH₃ | CH₃ | CH₃ | OCH₃ | |
| 74 | H | H | H | H | CH₃ | CH₃ | CH₃ | H | |
| 32 | H | H | H | H | H | H | OCH₃ | C₂H₅ | |
| 32 | H | H | H | H | H | H | OCH₃ | OC₂H₅ | |
| 32 | H | H | H | H | H | H | OCH₃ | CH₂OCH₃ | |
| 35 | H | H | H | H | H | — | CH₃ | C₂H₅ | |
| 35 | H | H | H | H | H | — | CH₃ | OC₂H₅ | |
| 35 | H | H | H | H | H | — | CH₃ | CH₂OCH₃ | |

TABLE V

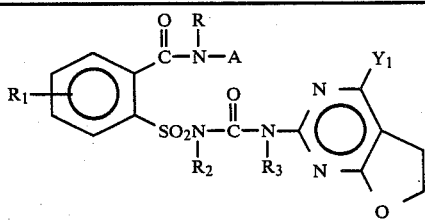

| A | R | R₁ | R₂ | R₃ | R₅ | R₆ | Y₁ | m.p. (°C.) |
|---|---|----|----|----|----|----|----|------------|
| 1 | H | H | H | H | H | H | CH₃ | |
| 1 | H | H | H | H | 4-CH₃ | H | CH₃ | |
| 2 | H | H | H | H | H | H | OCH₃ | |
| 2 | H | H | H | H | 5-CH₃ | H | CH₃ | |
| 3 | H | H | H | H | 2-CH₃ | 5-CH₃ | OCH₃ | |
| 3 | H | H | H | H | H | H | OCH₃ | |
| 4 | H | H | H | H | H | H | OCH₃ | |
| 5 | H | H | H | H | H | H | OCH₃ | |
| 5 | H | 5-Cl | H | H | H | H | OCH₃ | |
| 6 | H | H | H | H | H | H | CH₃ | |
| 6 | H | H | H | H | H | H | OCH₃ | |
| 7 | H | H | H | H | 3-CH₃ | 4-CH₃ | CH₃ | |
| 8 | H | 5-F | H | H | H | H | OCH₃ | |
| 8 | H | 5-Br | H | H | 4-CH₃ | H | OCH₃ | |
| 9 | H | H | H | H | H | H | CH₃ | |
| 10 | H | H | H | H | H | H | OCH₃ | |
| 11 | H | H | H | H | H | H | OCH₃ | |
| 12 | H | H | H | H | 5-SCH₃ | — | CH₃ | |
| 12 | H | H | H | H | 5-CH₃ | — | OCH₃ | |
| 12 | H | H | H | H | H | — | CH₃ | |
| 12 | H | H | H | H | H | — | OCH₃ | |
| 13 | H | H | H | H | 3-CH₃ | — | OCH₃ | |
| 14 | H | H | H | H | 3-CH₃ | — | CH₃ | |

TABLE V-continued

| A | R | R₁ | R₂ | R₃ | R₅ | R₆ | Y₁ | m.p. (°C.) |
|---|---|---|---|---|---|---|---|---|
| 15 | H | H | H | H | H | — | CH₃ | |
| 15 | H | H | H | H | CH₃ | — | OCH₃ | |
| 16 | H | H | H | H | H | — | OCH₃ | |
| 17 | H | 5-F | H | H | — | — | CH₃ | |
| 18 | H | H | H | H | CH₃ | — | CH₃ | |
| 19 | H | H | H | H | CH₃ | CH₃ | CH₃ | |
| 19 | H | H | H | H | CH₃ | CH₃ | OCH₃ | |
| 20 | H | H | H | H | H | H | CH₃ | |
| 21 | H | 5-OCH₃ | H | H | H | H | OCH₃ | |
| 22 | H | 5-CF₃ | H | H | H | H | CH₃ | |
| 22 | H | 5-NO₂ | H | H | H | — | OCH₃ | |
| 23 | H | H | H | H | H | — | OCH₃ | |
| 24 | H | H | H | H | 5-CH₃ | — | CH₃ | |
| 25 | H | H | H | H | H | — | CH₃ | |
| 25 | H | H | H | H | CH₃ | — | OCH₃ | |
| 26 | H | H | H | H | H | — | CH₃ | |
| 27 | H | 5-NO₂ | H | H | H | — | OCH₃ | |
| 28 | H | H | H | H | H | — | OCH₃ | |
| 29 | H | H | H | H | H | — | CH₃ | |
| 29 | H | H | H | H | H | — | OCH₃ | |
| 30 | H | H | H | H | H | — | CH₃ | |
| 31 | H | 5-Cl | H | H | H | — | CH₃ | |
| 31 | H | H | H | H | H | — | CH₃ | |
| 31 | H | H | H | H | H | — | OCH₃ | |
| 32 | H | H | H | H | H | H | CH₃ | |
| 32 | H | H | H | H | H | H | OCH₃ | |
| 32 | H | H | H | H | 4-CH₃ | H | OCH₃ | |
| 33 | H | H | H | H | H | — | CH₃ | |
| 33 | H | H | H | H | H | — | OCH₃ | |
| 33 | H | H | H | H | 2-CH₃ | — | OCH₃ | |
| 34 | H | H | H | H | 2-CH₃ | — | OCH₃ | |
| 34 | H | H | H | H | H | — | OCH₃ | |
| 34 | H | H | H | H | H | — | CH₃ | |
| 35 | H | H | H | H | H | — | CH₃ | |
| 35 | H | H | H | H | 5-CH₃ | — | OCH₃ | |
| 35 | H | H | H | H | H | — | OCH₃ | |
| 35 | CH₃ | H | H | H | H | — | OCH₃ | |
| 35 | H | H | CH₃ | H | H | — | OCH₃ | |
| 35 | H | H | H | CH₃ | H | — | OCH₃ | |
| 36 | H | H | H | H | H | — | CH₃ | |
| 36 | H | H | H | H | H | — | OCH₃ | |
| 37 | H | H | H | H | H | — | CH₃ | |
| 37 | H | H | H | H | H | — | OCH₃ | |
| 38 | H | H | H | H | H | — | OCH₃ | |
| 38 | H | H | H | H | CH₃ | — | OCH₃ | |
| 39 | H | H | H | H | H | — | CH₃ | |
| 39 | H | H | H | H | H | — | OCH₃ | |
| 40 | H | H | H | H | H | — | CH₃ | |
| 40 | H | H | H | H | H | — | OCH₃ | |
| 41 | H | H | H | H | 4-Cl | — | CH₃ | |
| 41 | H | H | H | H | 4-CN | — | CH₃ | |
| 41 | H | H | H | H | H | — | CH₃ | |
| 41 | H | H | H | H | H | — | OCH₃ | |
| 42 | H | H | H | H | 4-Cl | — | OCH₃ | |
| 42 | H | H | H | H | 5-CH₃ | — | OCH₃ | |
| 42 | H | H | H | H | H | — | CH₃ | |
| 42 | H | H | H | H | H | — | OCH₃ | |
| 43 | H | H | H | H | H | H | CH₃ | |
| 43 | H | H | H | H | H | H | OCH₃ | |
| 43 | H | H | H | H | 4-CH₃ | 6-CH₃ | OCH₃ | |
| 43 | H | H | H | H | 3-Cl | 5-CH₃ | OCH₃ | |
| 43 | H | H | H | H | 3-CH₃ | 5-CH₃ | OCH₃ | |
| 43 | H | H | H | H | 4-N(CH₃)₂ | H | OCH₃ | |
| 43 | H | H | H | H | 5-CN | H | OCH₃ | |
| 44 | H | H | H | H | H | H | CH₃ | |
| 44 | H | H | H | H | H | H | OCH₃ | |
| 45 | H | H | H | H | H | H | CH₃ | |
| 45 | H | H | H | H | H | H | OCH₃ | |
| 46 | H | H | H | H | H | H | CH₃ | |

TABLE V-continued

| A | R | R₁ | R₂ | R₃ | R₅ | R₆ | Y₁ | m.p. (°C.) |
|---|---|----|----|----|----|----|----|-----------|
| 46 | H | H | H | H | H | H | OCH₃ | |
| 46 | H | H | H | H | 5-CH₃ | H | OCH₃ | |
| 46 | H | H | H | H | 5-CH₃ | 6-CH₃ | OCH₃ | |
| 47 | H | H | H | H | H | H | CH₃ | |
| 47 | H | H | H | H | H | H | OCH₃ | |
| 47 | H | H | H | H | 6-CH₃ | H | OCH₃ | |
| 47 | H | H | H | H | 3-CH₃ | 6-CH₃ | OCH₃ | |
| 48 | H | H | H | H | 5-CH₃ | H | OCH₃ | |
| 48 | H | H | H | H | 5-Cl | H | OCH₃ | |
| 48 | H | H | H | H | H | H | CH₃ | |
| 48 | H | H | H | H | H | H | OCH₃ | |
| 49 | H | H | H | H | H | H | CH₃ | |
| 49 | H | H | H | H | H | H | OCH₃ | |
| 49 | H | H | H | H | 4-CH₃ | 6-CH₃ | CH₃ | |
| 49 | H | H | H | H | 4-CH₃ | 6-CH₃ | OCH₃ | |
| 49 | H | H | H | H | 4-OCH₃ | 6-OCH₃ | CH₃ | |
| 49 | H | H | H | H | 4-OCH₃ | 6-OCH₃ | OCH₃ | |
| 49 | H | H | H | H | 4-Cl | 6-Cl | OCH₃ | |
| 49 | H | H | H | H | 4-Cl | 4-N(CH₃)₂ | OCH₃ | |
| 49 | H | H | H | H | 4-OCH₃ | 6-SCH₃ | OCH₃ | |
| 49 | H | H | H | H | 4-Cl | 6-CN | OCH₃ | |
| 50 | H | H | H | H | H | H | CH₃ | |
| 50 | H | H | H | H | H | H | OCH₃ | |
| 50 | H | H | H | H | 2-CH₃ | 6-CH₃ | OCH₃ | |
| 50 | H | H | H | H | 2-CH₃ | 6-OCH₃ | OCH₃ | |
| 50 | H | H | H | H | 2-CH₃ | 6-Cl | OCH₃ | |
| 51 | H | H | H | H | H | H | CH₃ | |
| 51 | H | H | H | H | H | H | OCH₃ | |
| 51 | H | H | H | H | 2-CH₃ | H | OCH₃ | |
| 51 | H | H | H | H | 5-CH₃ | H | OCH₃ | |
| 51 | H | H | H | H | OCH₃ | H | OCH₃ | |
| 52 | H | H | H | H | H | H | CH₃ | |
| 52 | H | H | H | H | H | H | OCH₃ | |
| 52 | H | H | H | H | CH₃ | CH₃ | OCH₃ | |
| 52 | H | H | H | H | CH₃ | OCH₃ | OCH₃ | |
| 52 | H | H | H | H | OCH₃ | OCH₃ | OCH₃ | |
| 53 | H | H | H | H | H | H | CH₃ | |
| 53 | H | H | H | H | H | H | OCH₃ | |
| 53 | H | H | H | H | 5-CH₃ | 6-CH₃ | OCH₃ | |
| 54 | H | H | H | H | H | H | CH₃ | |
| 54 | H | H | H | H | H | H | OCH₃ | |
| 55 | H | H | H | H | H | H | CH₃ | |
| 55 | H | H | H | H | H | H | OCH₃ | |
| 56 | H | H | H | H | H | — | CH₃ | |
| 56 | H | H | H | H | H | — | OCH₃ | |
| 56 | H | H | H | H | 6-CH₃ | — | OCH₃ | |
| 57 | H | H | H | H | H | — | OCH₃ | |
| 57 | H | H | H | H | 4-CH₃ | — | OCH₃ | |
| 58 | H | H | H | H | H | — | OCH₃ | |
| 58 | H | H | H | H | 4-CH₃ | — | OCH₃ | |
| 59 | H | H | H | H | H | — | CH₃ | |
| 59 | H | H | H | H | H | — | OCH₃ | |
| 59 | H | H | H | H | 4-CH₃ | — | OCH₃ | |
| 59 | H | H | H | H | 5-CH₃ | — | OCH₃ | |
| 60 | H | H | H | H | 4-CH₃ | — | OCH₃ | |
| 61 | H | H | H | H | H | — | OCH₃ | |
| 61 | H | H | H | H | 5-CH₃ | — | OCH₃ | |
| 62 | H | H | H | H | H | — | CH₃ | |
| 62 | H | H | H | H | H | — | OCH₃ | |
| 63 | H | H | H | H | H | — | CH₃ | |
| 63 | H | H | H | H | H | — | OCH₃ | |
| 64 | H | H | H | H | H | — | CH₃ | |
| 64 | H | H | H | H | H | — | OCH₃ | |
| 65 | H | H | H | H | H | — | OCH₃ | |
| 66 | H | H | H | H | H | — | OCH₃ | |
| 67 | H | H | H | H | H | — | CH₃ | |
| 67 | H | H | H | H | H | — | OCH₃ | |
| 68 | H | H | H | H | H | — | CH₃ | |
| 68 | H | H | H | H | H | — | OCH₃ | |

TABLE V-continued

[Structure: R₁-phenyl with C(=O)-N(R)-A substituent, SO₂N(R₂)-C(=O)-N(R₃) linker to a pyridine fused with oxygen-containing ring bearing Y₁]

| A | R | R₁ | R₂ | R₃ | R₅ | R₆ | Y₁ | m.p. (°C.) |
|---|---|----|----|----|----|----|----|------------|
| 69 | H | H | H | H | H | — | CH₃ | |
| 69 | H | H | H | H | H | — | OCH₃ | |
| 70 | H | H | H | H | H | — | CH₃ | |
| 70 | H | H | H | H | H | — | OCH₃ | |
| 71 | H | H | H | H | H | H | CH₃ | |
| 71 | H | H | H | H | H | H | OCH₃ | |
| 71 | H | H | H | H | CH₃ | CH₃ | CH₃ | |
| 71 | H | H | H | H | CH₃ | CH₃ | OCH₃ | |
| 71 | H | H | H | H | CH₃ | OCH₃ | OCH₃ | |
| 71 | H | H | H | H | OCH₃ | OCH₃ | OCH₃ | |
| 72 | H | H | H | H | H | H | CH₃ | |
| 72 | H | H | H | H | H | H | OCH₃ | |
| 72 | H | H | H | H | CH₃ | CH₃ | CH₃ | |
| 72 | H | H | H | H | CH₃ | CH₃ | OCH₃ | |
| 72 | H | H | H | H | CH₃ | OCH₃ | OCH₃ | |
| 72 | H | H | H | H | OCH₃ | OCH₃ | OCH₃ | |
| 73 | H | H | H | H | H | H | CH₃ | |
| 73 | H | H | H | H | H | H | OCH₃ | |
| 73 | H | H | H | H | CH₃ | CH₃ | CH₃ | |
| 73 | H | H | H | H | CH₃ | CH₃ | OCH₃ | |
| 73 | H | H | H | H | CH₃ | OCH₃ | OCH₃ | |
| 73 | H | H | H | H | OCH₃ | OCH₃ | OCH₃ | |
| 74 | H | H | H | H | CH₃ | CH₃ | CH₃ | |
| 74 | H | H | H | H | CH₃ | CH₃ | OCH₃ | |
| 32 | H | H | H | H | H | H | Cl | |
| 32 | H | H | H | H | H | H | H | |
| 35 | H | H | H | H | H | — | Cl | |
| 35 | H | H | H | H | H | — | H | |

TABLE VI

[Structure: R₁-phenyl with C(=O)-N(R)-A substituent, SO₂N(R₂)-C(=O)-N(R₃) linker to a pyridine fused with oxygen-containing ring bearing Y₁]

| A | R | R₁ | R₂ | R₃ | R₅ | R₆ | Y₁ | m.p. (°C.) |
|---|---|----|----|----|----|----|----|------------|
| 1 | H | H | H | H | H | H | CH₃ | |
| 1 | H | H | H | H | 4-CH₃ | H | CH₃ | |
| 2 | H | H | H | H | H | H | OCH₃ | |
| 2 | H | H | H | H | 5-CH₃ | H | CH₃ | |
| 3 | H | H | H | H | 2-CH₃ | 5-CH₃ | OCH₃ | |
| 3 | H | H | H | H | H | H | OCH₃ | |
| 4 | H | H | H | H | H | H | OCH₃ | |
| 5 | H | H | H | H | H | H | OCH₃ | |
| 5 | H | 5-Cl | H | H | H | H | OCH₃ | |
| 6 | H | H | H | H | H | H | CH₃ | |
| 6 | H | H | H | H | H | H | OCH₃ | |
| 7 | H | H | H | H | 3-CH₃ | 4-CH₃ | CH₃ | |
| 8 | H | 5-F | H | H | H | H | OCH₃ | |
| 8 | H | 5-Br | H | H | 4-CH₃ | H | OCH₃ | |
| 9 | H | H | H | H | H | H | CH₃ | |
| 10 | H | H | H | H | H | H | OCH₃ | |
| 11 | H | H | H | H | H | H | OCH₃ | |
| 12 | H | H | H | H | 5-SCH₃ | — | CH₃ | |
| 12 | H | H | H | H | 5-CH₃ | — | OCH₃ | |
| 12 | H | H | H | H | H | — | CH₃ | |
| 12 | H | H | H | H | H | — | OCH₃ | |
| 13 | H | H | H | H | 3-CH₃ | — | OCH₃ | |
| 14 | H | H | H | H | 3-CH₃ | — | CH₃ | |
| 15 | H | H | H | H | H | — | CH₃ | |
| 15 | H | H | H | H | CH₃ | — | OCH₃ | |

TABLE VI-continued

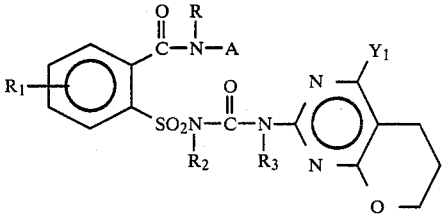

| A | R | R₁ | R₂ | R₃ | R₅ | R₆ | Y₁ | m.p. (°C.) |
|---|---|---|---|---|---|---|---|---|
| 16 | H | H | H | H | H | — | OCH₃ | |
| 17 | H | 5-F | H | H | — | — | CH₃ | |
| 18 | H | H | H | H | CH₃ | — | CH₃ | |
| 19 | H | H | H | H | CH₃ | CH₃ | CH₃ | |
| 19 | H | H | H | H | CH₃ | CH₃ | OCH₃ | |
| 20 | H | H | H | H | H | H | CH₃ | |
| 21 | H | 5-OCH₃ | H | H | H | H | OCH₃ | |
| 22 | H | 5-CF₃ | H | H | H | H | CH₃ | |
| 22 | H | 5-NO₂ | H | H | H | — | OCH₃ | |
| 23 | H | H | H | H | H | — | OCH₃ | |
| 24 | H | H | H | H | 5-CH₃ | — | CH₃ | |
| 25 | H | H | H | H | H | — | CH₃ | |
| 25 | H | H | H | H | CH₃ | — | OCH₃ | |
| 26 | H | H | H | H | H | — | CH₃ | |
| 27 | H | 5-NO₂ | H | H | H | — | OCH₃ | |
| 28 | H | H | H | H | H | — | OCH₃ | |
| 29 | H | H | H | H | H | — | CH₃ | |
| 29 | H | H | H | H | H | — | OCH₃ | |
| 30 | H | H | H | H | H | — | CH₃ | |
| 31 | H | 5-Cl | H | H | H | — | CH₃ | |
| 31 | H | H | H | H | H | — | CH₃ | |
| 31 | H | H | H | H | H | — | OCH₃ | |
| 32 | H | H | H | H | H | H | CH₃ | |
| 32 | H | H | H | H | H | H | OCH₃ | |
| 32 | H | H | H | H | 4-CH₃ | H | OCH₃ | |
| 33 | H | H | H | H | H | — | CH₃ | |
| 33 | H | H | H | H | H | — | OCH₃ | |
| 33 | H | H | H | H | 2-CH₃ | — | OCH₃ | |
| 34 | H | H | H | H | 2-CH₃ | — | OCH₃ | |
| 34 | H | H | H | H | H | — | OCH₃ | |
| 34 | H | H | H | H | H | — | CH₃ | |
| 35 | H | H | H | H | H | — | CH₃ | |
| 35 | H | H | H | H | 5-CH₃ | — | OCH₃ | |
| 35 | H | H | H | H | H | — | OCH₃ | |
| 35 | CH₃ | H | H | H | H | — | OCH₃ | |
| 35 | H | H | CH₃ | H | H | — | OCH₃ | |
| 35 | H | H | H | CH₃ | H | — | OCH₃ | |
| 36 | H | H | H | H | H | — | CH₃ | |
| 36 | H | H | H | H | H | — | OCH₃ | |
| 37 | H | H | H | H | H | — | CH₃ | |
| 37 | H | H | H | H | H | — | OCH₃ | |
| 38 | H | H | H | H | H | — | OCH₃ | |
| 38 | H | H | H | H | CH₃ | — | OCH₃ | |
| 39 | H | H | H | H | H | — | CH₃ | |
| 39 | H | H | H | H | H | — | OCH₃ | |
| 40 | H | H | H | H | H | — | CH₃ | |
| 40 | H | H | H | H | H | — | OCH₃ | |
| 41 | H | H | H | H | 4-Cl | — | CH₃ | |
| 41 | H | H | H | H | 4-CN | — | CH₃ | |
| 41 | H | H | H | H | H | — | CH₃ | |
| 41 | H | H | H | H | H | — | OCH₃ | |
| 42 | H | H | H | H | 4-Cl | — | OCH₃ | |
| 42 | H | H | H | H | 5-CH₃ | — | OCH₃ | |
| 42 | H | H | H | H | H | — | CH₃ | |
| 42 | H | H | H | H | H | — | OCH₃ | |
| 43 | H | H | H | H | H | H | CH₃ | |
| 43 | H | H | H | H | H | H | OCH₃ | |
| 43 | H | H | H | H | 4-CH₃ | 6-CH₃ | OCH₃ | |
| 43 | H | H | H | H | 3-Cl | 5-CH₃ | OCH₃ | |
| 43 | H | H | H | H | 3-CH₃ | 5-CH₃ | OCH₃ | |
| 43 | H | H | H | H | 4-N(CH₃)₂ | H | OCH₃ | |
| 43 | H | H | H | H | 5-CN | H | OCH₃ | |
| 44 | H | H | H | H | H | H | CH₃ | |
| 44 | H | H | H | H | H | H | OCH₃ | |
| 45 | H | H | H | H | H | H | CH₃ | |
| 45 | H | H | H | H | H | H | OCH₃ | |
| 46 | H | H | H | H | H | H | CH₃ | |
| 46 | H | H | H | H | H | H | OCH₃ | |
| 46 | H | H | H | H | 5-CH₃ | H | OCH₃ | |

TABLE VI-continued

| A | R | R₁ | R₂ | R₃ | R₅ | R₆ | Y₁ | m.p. (°C.) |
|---|---|----|----|----|----|----|----|------------|
| 46 | H | H | H | H | 5-CH₃ | 6-CH₃ | OCH₃ | |
| 47 | H | H | H | H | H | H | CH₃ | |
| 47 | H | H | H | H | H | H | OCH₃ | |
| 47 | H | H | H | H | 6-CH₃ | H | OCH₃ | |
| 47 | H | H | H | H | 3-CH₃ | 6-CH₃ | OCH₃ | |
| 48 | H | H | H | H | 5-CH₃ | H | OCH₃ | |
| 48 | H | H | H | H | 5-Cl | H | OCH₃ | |
| 48 | H | H | H | H | H | H | CH₃ | |
| 48 | H | H | H | H | H | H | OCH₃ | |
| 49 | H | H | H | H | H | H | CH₃ | |
| 49 | H | H | H | H | H | H | OCH₃ | |
| 49 | H | H | H | H | 4-CH₃ | 6-CH₃ | CH₃ | |
| 49 | H | H | H | H | 4-CH₃ | 6-CH₃ | OCH₃ | |
| 49 | H | H | H | H | 4-OCH₃ | 6-OCH₃ | CH₃ | |
| 49 | H | H | H | H | 4-OCH₃ | 6-OCH₃ | OCH₃ | |
| 49 | H | H | H | H | 4-Cl | 6-Cl | OCH₃ | |
| 49 | H | H | H | H | 4-Cl | 4-N(CH₃)₂ | OCH₃ | |
| 49 | H | H | H | H | 4-OCH₃ | 6-SCH₃ | OCH₃ | |
| 49 | H | H | H | H | 4-Cl | 6-CN | OCH₃ | |
| 50 | H | H | H | H | H | H | CH₃ | |
| 50 | H | H | H | H | H | H | OCH₃ | |
| 50 | H | H | H | H | 2-CH₃ | 6-CH₃ | OCH₃ | |
| 50 | H | H | H | H | 2-CH₃ | 6-OCH₃ | OCH₃ | |
| 50 | H | H | H | H | 2-CH₃ | 6-Cl | OCH₃ | |
| 51 | H | H | H | H | H | H | CH₃ | |
| 51 | H | H | H | H | H | H | OCH₃ | |
| 51 | H | H | H | H | 2-CH₃ | H | OCH₃ | |
| 51 | H | H | H | H | 5-CH₃ | H | OCH₃ | |
| 51 | H | H | H | H | OCH₃ | H | OCH₃ | |
| 52 | H | H | H | H | H | H | CH₃ | |
| 52 | H | H | H | H | H | H | OCH₃ | |
| 52 | H | H | H | H | CH₃ | CH₃ | OCH₃ | |
| 52 | H | H | H | H | CH₃ | OCH₃ | OCH₃ | |
| 52 | H | H | H | H | OCH₃ | OCH₃ | OCH₃ | |
| 53 | H | H | H | H | H | H | CH₃ | |
| 53 | H | H | H | H | H | H | OCH₃ | |
| 53 | H | H | H | H | 5-CH₃ | 6-CH₃ | OCH₃ | |
| 54 | H | H | H | H | H | H | CH₃ | |
| 54 | H | H | H | H | H | H | OCH₃ | |
| 55 | H | H | H | H | H | H | CH₃ | |
| 55 | H | H | H | H | H | H | OCH₃ | |
| 56 | H | H | H | H | H | — | CH₃ | |
| 56 | H | H | H | H | H | — | OCH₃ | |
| 56 | H | H | H | H | 6-CH₃ | — | OCH₃ | |
| 57 | H | H | H | H | H | — | OCH₃ | |
| 57 | H | H | H | H | 4-CH₃ | — | OCH₃ | |
| 58 | H | H | H | H | H | — | OCH₃ | |
| 58 | H | H | H | H | 4-CH₃ | — | OCH₃ | |
| 59 | H | H | H | H | H | — | CH₃ | |
| 59 | H | H | H | H | H | — | OCH₃ | |
| 59 | H | H | H | H | 4-CH₃ | — | OCH₃ | |
| 59 | H | H | H | H | 5-CH₃ | — | OCH₃ | |
| 60 | H | H | H | H | 4-CH₃ | — | OCH₃ | |
| 61 | H | H | H | H | H | — | OCH₃ | |
| 61 | H | H | H | H | 5-CH₃ | — | OCH₃ | |
| 62 | H | H | H | H | H | — | CH₃ | |
| 62 | H | H | H | H | H | — | OCH₃ | |
| 63 | H | H | H | H | H | — | CH₃ | |
| 63 | H | H | H | H | H | — | OCH₃ | |
| 64 | H | H | H | H | H | — | CH₃ | |
| 64 | H | H | H | H | H | — | OCH₃ | |
| 65 | H | H | H | H | H | — | OCH₃ | |
| 66 | H | H | H | H | H | — | OCH₃ | |
| 67 | H | H | H | H | H | — | CH₃ | |
| 67 | H | H | H | H | H | — | OCH₃ | |
| 68 | H | H | H | H | H | — | CH₃ | |
| 68 | H | H | H | H | H | — | OCH₃ | |
| 69 | H | H | H | H | H | — | CH₃ | |
| 69 | H | H | H | H | H | — | OCH₃ | |

TABLE VI-continued

[Structure: R₁-substituted benzene with C(O)-N(R)-A group, SO₂N(R₂)-C(O)-N(R₃)-pyrimidine with Y₁ and fused oxygen-containing ring]

| A | R | R₁ | R₂ | R₃ | R₅ | R₆ | Y₁ | m.p. (°C.) |
|---|---|----|----|----|----|----|----|------------|
| 70 | H | H | H | H | H | — | CH₃ | |
| 70 | H | H | H | H | H | — | OCH₃ | |
| 71 | H | H | H | H | H | H | CH₃ | |
| 71 | H | H | H | H | H | H | OCH₃ | |
| 71 | H | H | H | H | CH₃ | CH₃ | CH₃ | |
| 71 | H | H | H | H | CH₃ | CH₃ | OCH₃ | |
| 71 | H | H | H | H | CH₃ | OCH₃ | OCH₃ | |
| 71 | H | H | H | H | OCH₃ | OCH₃ | OCH₃ | |
| 72 | H | H | H | H | H | H | CH₃ | |
| 72 | H | H | H | H | H | H | OCH₃ | |
| 72 | H | H | H | H | CH₃ | CH₃ | CH₃ | |
| 72 | H | H | H | H | CH₃ | CH₃ | OCH₃ | |
| 72 | H | H | H | H | CH₃ | OCH₃ | OCH₃ | |
| 72 | H | H | H | H | OCH₃ | OCH₃ | OCH₃ | |
| 73 | H | H | H | H | H | H | CH₃ | |
| 73 | H | H | H | H | H | H | OCH₃ | |
| 73 | H | H | H | H | CH₃ | CH₃ | CH₃ | |
| 73 | H | H | H | H | CH₃ | CH₃ | OCH₃ | |
| 73 | H | H | H | H | CH₃ | OCH₃ | OCH₃ | |
| 73 | H | H | H | H | OCH₃ | OCH₃ | OCH₃ | |
| 74 | H | H | H | H | CH₃ | CH₃ | CH₃ | |
| 74 | H | H | H | H | CH₃ | CH₃ | OCH₃ | |
| 32 | H | H | H | H | H | H | Cl | |
| 32 | H | H | H | H | H | H | H | |
| 35 | H | H | H | H | H | — | Cl | |
| 35 | H | H | H | H | H | — | H | |

TABLE VII

[Structure: R₁-substituted benzene with C(O)-N(R)-A group, SO₂N(R₂)-C(O)-N(R₃)-pyrimidine fused with furan ring bearing CH₃ and Y₁]

| A | R | R₁ | R₂ | R₃ | R₅ | R₆ | Y₁ | m.p. (°C.) |
|---|---|----|----|----|----|----|----|------------|
| 1 | H | H | H | H | H | H | CH₃ | |
| 1 | H | H | H | H | 4-CH₃ | H | CH₃ | |
| 2 | H | H | H | H | H | H | OCH₃ | |
| 2 | H | H | H | H | 5-CH₃ | H | CH₃ | |
| 3 | H | H | H | H | 2-CH₃ | 5-CH₃ | OCH₃ | |
| 3 | H | H | H | H | H | H | OCH₃ | |
| 4 | H | H | H | H | H | H | OCH₃ | |
| 5 | H | H | H | H | H | H | OCH₃ | |
| 5 | H | 5-Cl | H | H | H | H | OCH₃ | |
| 6 | H | H | H | H | H | H | CH₃ | |
| 6 | H | H | H | H | H | H | OCH₃ | |
| 7 | H | H | H | H | 3-CH₃ | 4-CH₃ | CH₃ | |
| 8 | H | 5-F | H | H | H | H | OCH₃ | |
| 8 | H | 5-Br | H | H | 4-CH₃ | H | OCH₃ | |
| 9 | H | H | H | H | H | H | CH₃ | |
| 10 | H | H | H | H | H | H | OCH₃ | |
| 11 | H | H | H | H | H | H | OCH₃ | |
| 12 | H | H | H | H | 5-SCH₃ | — | CH₃ | |
| 12 | H | H | H | H | 5-CH₃ | — | OCH₃ | |
| 12 | H | H | H | H | H | — | CH₃ | |
| 12 | H | H | H | H | H | — | OCH₃ | |
| 13 | H | H | H | H | 3-CH₃ | — | OCH₃ | |
| 14 | H | H | H | H | 3-CH₃ | — | CH₃ | |
| 15 | H | H | H | H | H | — | CH₃ | |
| 15 | H | H | H | H | CH₃ | — | OCH₃ | |
| 16 | H | H | H | H | H | — | OCH₃ | |
| 17 | H | 5-F | H | H | — | — | CH₃ | |

TABLE VII-continued

| A | R | R₁ | R₂ | R₃ | R₅ | R₆ | Y₁ | m.p. (°C.) |
|---|---|---|---|---|---|---|---|---|
| 18 | H | H | H | H | CH₃ | — | CH₃ | |
| 19 | H | H | H | H | CH₃ | CH₃ | CH₃ | |
| 19 | H | H | H | H | CH₃ | CH₃ | OCH₃ | |
| 20 | H | H | H | H | H | H | CH₃ | |
| 21 | H | 5-OCH₃ | H | H | H | H | OCH₃ | |
| 22 | H | 5-CF₃ | H | H | H | H | CH₃ | |
| 22 | H | 5-NO₂ | H | H | H | — | OCH₃ | |
| 23 | H | H | H | H | H | — | OCH₃ | |
| 24 | H | H | H | H | 5-CH₃ | — | CH₃ | |
| 25 | H | H | H | H | H | — | CH₃ | |
| 25 | H | H | H | H | CH₃ | — | OCH₃ | |
| 26 | H | H | H | H | H | — | CH₃ | |
| 27 | H | 5-NO₂ | H | H | H | — | OCH₃ | |
| 28 | H | H | H | H | H | — | OCH₃ | |
| 29 | H | H | H | H | H | — | CH₃ | |
| 29 | H | H | H | H | H | — | OCH₃ | |
| 30 | H | H | H | H | H | — | CH₃ | |
| 31 | H | 5-Cl | H | H | H | — | CH₃ | |
| 31 | H | H | H | H | H | — | CH₃ | |
| 31 | H | H | H | H | H | — | OCH₃ | |
| 32 | H | H | H | H | H | H | CH₃ | |
| 32 | H | H | H | H | H | H | OCH₃ | |
| 32 | H | H | H | H | 4-CH₃ | H | OCH₃ | |
| 33 | H | H | H | H | H | — | CH₃ | |
| 33 | H | H | H | H | H | — | OCH₃ | |
| 33 | H | H | H | H | 2-CH₃ | — | OCH₃ | |
| 34 | H | H | H | H | 2-CH₃ | — | OCH₃ | |
| 34 | H | H | H | H | H | — | OCH₃ | |
| 34 | H | H | H | H | H | — | CH₃ | |
| 35 | H | H | H | H | H | — | CH₃ | |
| 35 | H | H | H | H | 5-CH₃ | — | OCH₃ | |
| 35 | H | H | H | H | H | — | OCH₃ | |
| 35 | CH₃ | H | H | H | H | — | OCH₃ | |
| 35 | H | H | CH₃ | H | H | — | OCH₃ | |
| 35 | H | H | H | CH₃ | H | — | OCH₃ | |
| 36 | H | H | H | H | H | — | CH₃ | |
| 36 | H | H | H | H | H | — | OCH₃ | |
| 37 | H | H | H | H | H | — | CH₃ | |
| 37 | H | H | H | H | H | — | OCH₃ | |
| 38 | H | H | H | H | H | — | OCH₃ | |
| 38 | H | H | H | H | CH₃ | — | OCH₃ | |
| 39 | H | H | H | H | H | — | CH₃ | |
| 39 | H | H | H | H | H | — | OCH₃ | |
| 40 | H | H | H | H | H | — | CH₃ | |
| 40 | H | H | H | H | H | — | OCH₃ | |
| 41 | H | H | H | H | 4-Cl | — | CH₃ | |
| 41 | H | H | H | H | 4-CN | — | CH₃ | |
| 41 | H | H | H | H | H | — | CH₃ | |
| 41 | H | H | H | H | H | — | OCH₃ | |
| 42 | H | H | H | H | 4-Cl | — | OCH₃ | |
| 42 | H | H | H | H | 5-CH₃ | — | OCH₃ | |
| 42 | H | H | H | H | H | — | CH₃ | |
| 42 | H | H | H | H | H | — | OCH₃ | |
| 43 | H | H | H | H | H | H | CH₃ | |
| 43 | H | H | H | H | H | H | OCH₃ | |
| 43 | H | H | H | H | 4-CH₃ | 6-CH₃ | OCH₃ | |
| 43 | H | H | H | H | 3-Cl | 5-CH₃ | OCH₃ | |
| 43 | H | H | H | H | 3-CH₃ | 5-CH₃ | OCH₃ | |
| 43 | H | H | H | H | 4-N(CH₃)₂ | H | OCH₃ | |
| 43 | H | H | H | H | 5-CN | H | OCH₃ | |
| 44 | H | H | H | H | H | H | CH₃ | |
| 44 | H | H | H | H | H | H | OCH₃ | |
| 45 | H | H | H | H | H | H | CH₃ | |
| 45 | H | H | H | H | H | H | OCH₃ | |
| 46 | H | H | H | H | H | H | CH₃ | |
| 46 | H | H | H | H | H | H | OCH₃ | |
| 46 | H | H | H | H | 5-CH₃ | H | OCH₃ | |
| 46 | H | H | H | H | 5-CH₃ | 6-CH₃ | OCH₃ | |
| 47 | H | H | H | H | H | H | CH₃ | |

TABLE VII-continued

| A | R | R₁ | R₂ | R₃ | R₅ | R₆ | Y₁ | m.p. (°C.) |
|---|---|----|----|----|----|----|----|------------|
| 47 | H | H | H | H | H | H | OCH₃ | |
| 47 | H | H | H | H | 6-CH₃ | H | OCH₃ | |
| 47 | H | H | H | H | 3-CH₃ | 6-CH₃ | OCH₃ | |
| 48 | H | H | H | H | 5-CH₃ | H | OCH₃ | |
| 48 | H | H | H | H | 5-Cl | H | OCH₃ | |
| 48 | H | H | H | H | H | H | CH₃ | |
| 48 | H | H | H | H | H | H | OCH₃ | |
| 49 | H | H | H | H | H | H | CH₃ | |
| 49 | H | H | H | H | H | H | OCH₃ | |
| 49 | H | H | H | H | 4-CH₃ | 6-CH₃ | CH₃ | |
| 49 | H | H | H | H | 4-CH₃ | 6-CH₃ | OCH₃ | |
| 49 | H | H | H | H | 4-OCH₃ | 6-OCH₃ | CH₃ | |
| 49 | H | H | H | H | 4-OCH₃ | 6-OCH₃ | OCH₃ | |
| 49 | H | H | H | H | 4-Cl | 6-Cl | OCH₃ | |
| 49 | H | H | H | H | 4-Cl | 4-N(CH₃)₂ | OCH₃ | |
| 49 | H | H | H | H | 4-OCH₃ | 6-SCH₃ | OCH₃ | |
| 49 | H | H | H | H | 4-Cl | 6-CN | OCH₃ | |
| 50 | H | H | H | H | H | H | CH₃ | |
| 50 | H | H | H | H | H | H | OCH₃ | |
| 50 | H | H | H | H | 2-CH₃ | 6-CH₃ | OCH₃ | |
| 50 | H | H | H | H | 2-CH₃ | 6-OCH₃ | OCH₃ | |
| 50 | H | H | H | H | 2-CH₃ | 6-Cl | OCH₃ | |
| 51 | H | H | H | H | H | H | CH₃ | |
| 51 | H | H | H | H | H | H | OCH₃ | |
| 51 | H | H | H | H | 2-CH₃ | H | OCH₃ | |
| 51 | H | H | H | H | 5-CH₃ | H | OCH₃ | |
| 51 | H | H | H | H | OCH₃ | H | OCH₃ | |
| 52 | H | H | H | H | H | H | CH₃ | |
| 52 | H | H | H | H | H | H | OCH₃ | |
| 52 | H | H | H | H | CH₃ | CH₃ | OCH₃ | |
| 52 | H | H | H | H | CH₃ | OCH₃ | OCH₃ | |
| 52 | H | H | H | H | OCH₃ | OCH₃ | OCH₃ | |
| 53 | H | H | H | H | H | H | CH₃ | |
| 53 | H | H | H | H | H | H | OCH₃ | |
| 53 | H | H | H | H | 5-CH₃ | 6-CH₃ | OCH₃ | |
| 54 | H | H | H | H | H | H | CH₃ | |
| 54 | H | H | H | H | H | H | OCH₃ | |
| 55 | H | H | H | H | H | H | CH₃ | |
| 55 | H | H | H | H | H | H | OCH₃ | |
| 56 | H | H | H | H | H | — | CH₃ | |
| 56 | H | H | H | H | H | — | OCH₃ | |
| 56 | H | H | H | H | 6-CH₃ | — | OCH₃ | |
| 57 | H | H | H | H | H | — | OCH₃ | |
| 57 | H | H | H | H | 4-CH₃ | — | OCH₃ | |
| 58 | H | H | H | H | H | — | OCH₃ | |
| 58 | H | H | H | H | 4-CH₃ | — | OCH₃ | |
| 59 | H | H | H | H | H | — | CH₃ | |
| 59 | H | H | H | H | H | — | OCH₃ | |
| 59 | H | H | H | H | 4-CH₃ | — | OCH₃ | |
| 59 | H | H | H | H | 5-CH₃ | — | OCH₃ | |
| 60 | H | H | H | H | 4-CH₃ | — | OCH₃ | |
| 61 | H | H | H | H | H | — | OCH₃ | |
| 61 | H | H | H | H | 5-CH₃ | — | OCH₃ | |
| 62 | H | H | H | H | H | — | CH₃ | |
| 62 | H | H | H | H | H | — | OCH₃ | |
| 63 | H | H | H | H | H | — | CH₃ | |
| 63 | H | H | H | H | H | — | OCH₃ | |
| 64 | H | H | H | H | H | — | CH₃ | |
| 64 | H | H | H | H | H | — | OCH₃ | |
| 65 | H | H | H | H | H | — | OCH₃ | |
| 66 | H | H | H | H | H | — | OCH₃ | |
| 67 | H | H | H | H | H | — | CH₃ | |
| 67 | H | H | H | H | H | — | OCH₃ | |
| 68 | H | H | H | H | H | — | CH₃ | |
| 68 | H | H | H | H | H | — | OCH₃ | |
| 69 | H | H | H | H | H | — | CH₃ | |
| 69 | H | H | H | H | H | — | OCH₃ | |
| 70 | H | H | H | H | H | — | CH₃ | |
| 70 | H | H | H | H | H | — | OCH₃ | |

TABLE VII-continued

![Structure with R, R1, R2, R3, R5, R6, Y1 substituents on the depicted scaffold]

| A | R | $R_1$ | $R_2$ | $R_3$ | $R_5$ | $R_6$ | $Y_1$ | m.p. (°C.) |
|---|---|---|---|---|---|---|---|---|
| 71 | H | H | H | H | H | H | $CH_3$ | |
| 71 | H | H | H | H | H | H | $OCH_3$ | |
| 71 | H | H | H | H | $CH_3$ | $CH_3$ | $CH_3$ | |
| 71 | H | H | H | H | $CH_3$ | $CH_3$ | $OCH_3$ | |
| 71 | H | H | H | H | $CH_3$ | $OCH_3$ | $OCH_3$ | |
| 71 | H | H | H | H | $OCH_3$ | $OCH_3$ | $OCH_3$ | |
| 72 | H | H | H | H | H | H | $CH_3$ | |
| 72 | H | H | H | H | H | H | $OCH_3$ | |
| 72 | H | H | H | H | $CH_3$ | $CH_3$ | $CH_3$ | |
| 72 | H | H | H | H | $CH_3$ | $CH_3$ | $OCH_3$ | |
| 72 | H | H | H | H | $CH_3$ | $OCH_3$ | $OCH_3$ | |
| 72 | H | H | H | H | $OCH_3$ | $OCH_3$ | $OCH_3$ | |
| 73 | H | H | H | H | H | H | $CH_3$ | |
| 73 | H | H | H | H | H | H | $OCH_3$ | |
| 73 | H | H | H | H | $CH_3$ | $CH_3$ | $CH_3$ | |
| 73 | H | H | H | H | $CH_3$ | $CH_3$ | $OCH_3$ | |
| 73 | H | H | H | H | $CH_3$ | $OCH_3$ | $OCH_3$ | |
| 73 | H | H | H | H | $OCH_3$ | $OCH_3$ | $OCH_3$ | |
| 74 | H | H | H | H | $CH_3$ | $CH_3$ | $CH_3$ | |
| 74 | H | H | H | H | $CH_3$ | $CH_3$ | $OCH_3$ | |
| 32 | H | H | H | H | H | H | Cl | |
| 32 | H | H | H | H | H | H | H | |
| 35 | H | H | H | H | H | — | Cl | |
| 35 | H | H | H | H | H | — | H | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE VIII

| | Active Ingredient | Weight Percent* Diluent(s) | Surfactant(s) |
|---|---|---|---|
| Wettable Powders | 20-90 | 0-74 | 1-10 |
| Oil Suspensions, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

* Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley & Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 6

Wettable Powder

| | |
|---|---|
| 2-[[(4,6-dimethoxypyrimidin-2-yl)aminocarbonyl]-aminsulfonyl]-N—(4,6-dimethylpyrimidin-2-yl)-benzamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 7

Wettable Powder

| | |
|---|---|
| 2-[[(4-methoxy-6-methylpyrimidin-2-yl)aminocarbonyl]-aminosulfonyl]-N—(thiazol-2-yl)benzamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 8

Granule

| | |
|---|---|
| Wettable Powder of Example 7 | 5% |
| attapulgite granules (U.S.S. 20–40 mesh; 0.84–0.42 mm) | 95% |

A slurry of wettable powder containing ≈25% solids is sprayed on the surface of attapulgite granules in a double-cone blender. The granules are dried and packaged.

EXAMPLE 9

Extruded Pellet

| | |
|---|---|
| 2-[[(4-methoxy-6-methylpyrimidin-2-yl)aminocarbonyl]-aminosulfonyl]-N—(2-pyridinyl)benzamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 10

Oil Suspension

| | |
|---|---|
| 2-[[(4-methoxy-6-methylpyrimidin-2-yl)aminocarbonyl]aminosulfonyl]-N—(1,3,4-thiadiazol-2-yl)-benzamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 11

Wettable Powder

| | |
|---|---|
| N—(3,4-dimethylisoxazol-5-yl)-2-[[(4-methoxy-6-methylpyrimidin-2-yl)aminocarbonyl]aminosulfonyl]-benzamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 12

Low Strength Granule

| | |
|---|---|
| 2-[[(4-methoxy-6-methyl-1,3,5-triazin-2-yl)aminocarbonyl]aminosulfonyl]-N—(1-methyl-1H—pyrazol-3-yl)benzamide | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 13

Aqueous Suspension

| | |
|---|---|
| N—(3,4-dimethylisoxazol-5-yl)-2-[[(4-methoxy-6-methyl-pyrimidin-2-yl)aminocarbonyl]aminosulfonyl]- | 40% |

-continued

| | |
|---|---|
| benzamide | |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 14

Solution

| | |
|---|---|
| 2-[[(4,6-dimethoxypyrimidin-2-yl)aminocarbonyl]-aminosulfonyl]-N—(1,2,4-triazol-3-yl)-benzamide, sodium salt | 5% |
| water | 95% |

The salt is added directly to the water with stirring to produce the solution, which may then be packaged for use.

EXAMPLE 15

Low Strength Granule

| | |
|---|---|
| 2-[[(4-methoxy-6-methylpyrimidin-2-yl)aminocarbonyl]-aminosulfonyl]-N—(thiazol-2-yl)benzamide | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 16

Granule

| | |
|---|---|
| 2-[[(4-methoxy-6-methyl-1,3,5-triazin-2-yl)amino-carbonyl]aminosulfonyl]-N—1-methyl-1H—pyrazol-3-yl)benzamide | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 17

High Strength Concentrate

| | |
|---|---|
| 2-[[(4,6-dimethylpyrimidin-2-yl)aminocarbonyl]-aminosulfonyl]-N—(1,2,4-triazol-3-yl)-benzamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 18

Wettable Powder

| | |
|---|---|
| 2-[[(4-methoxy-6-methylpyrimidin-2-yl)aminocarbonyl]-aminosulfonyl]-N—(2-pyridinyl)benzamide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 19

Wettable Powder

| | |
|---|---|
| 2-[[(4-methoxy-6-methylpyrimidin-2-yl)aminocarbonyl]aminosulfonyl]-N—(1,3,4-thiadiazol-2-yl)-benzamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 20

Oil Suspension

| | |
|---|---|
| 2-[[(4,6-dimethoxypyrimidin-2-yl)aminocarbonyl]-aminosulfonyl]-N—(4,6-dimethylpyrimidin-2-yl)-benzamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

Utility

The compounds of the present invention are powerful herbicides. They have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures.

Some of the compounds are useful for the selective control of weeds in crops such as wheat and alfalfa.

The rates of application for the compounds of the invention are determined by a number of factors, including their use as selective or general herbicides, the crop species involved, the types of weeds to be controlled, weather and climate, formulations selected, mode of application, amount of foliage present, etc. In general terms, the subject compounds should be applied at levels of around 0.125 to 10 kg/ha, the lower rates being suggested for use on lighter soils and/or those having a low organic matter content, or for situations where only short-term persistence is required.

The compounds of the invention may be used in combination with any other commercial herbicide examples of which are those of the triazine, triazole, uracil, urea, amide, diphenylether, carbamate and bipyridylium types.

The herbicidal properties of the subject compounds were discovered in a number of greenhouse tests. The test procedures and results follow.

Test A

Seeds of crabgrass (Digitaria sp. ), barnyardgrass (*Echinochloa crusgalli*), wild oats (*Avena fatua*), cassia (*Cassia tora*), morningglory (Ipomoea sp.), cocklebur (Xanthium sp.), sorghum, corn, soybean, rice, wheat and nutsedge tubers (*Cyperus rotundus*) were planted in a growth medium and treated pre-emergence with the chemicals dissolved in a non-phytotoxic solvent. At the same time, cotton having five leaves (including cotyledonary ones), bush beans with the third trifoliolate leaf expanding, crabgrass, barnyardgrass and wild oats with two leaves, cassia with three leaves (including cotyledonary ones), morningglory and cocklebur with four leaves (including the cotyledonary ones), sorghum and corn with four leaves, soybean with two cotyledonary leaves, rice with three leaves, wheat with one leaf, and nutsedge with three to five leaves were sprayed. Treated plants and controls were maintained in a greenhouse for sixteen days, whereupon all species were compared to controls and visually rated for response to treatment.

The ratings are based on a numerical scale extending from 0=no injury, to 10=complete kill. The accompanying descriptive symbols have the following meanings:
C=chlorosis/necrosis;
D=defoliation;
E=emergence inhibition;
G=growth retardation;
H=formative effects;
I=increased chlorophyl;
S=albinism;
U=unusual pigmentation;
X=axillary stimulation; and
6Y=abscised buds or flowers.

The ratings for the compounds tested by this procedure are presented in Table A.

Some of the compounds included in this table, e.g. compounds 1, 3, 4 and 6, were relatively inactive at the very low rates of applications selected, i.e. 0.05 kg/ha. It can reasonably be expected that they would have performed better at higher treatment levels.

TABLE A
Structures

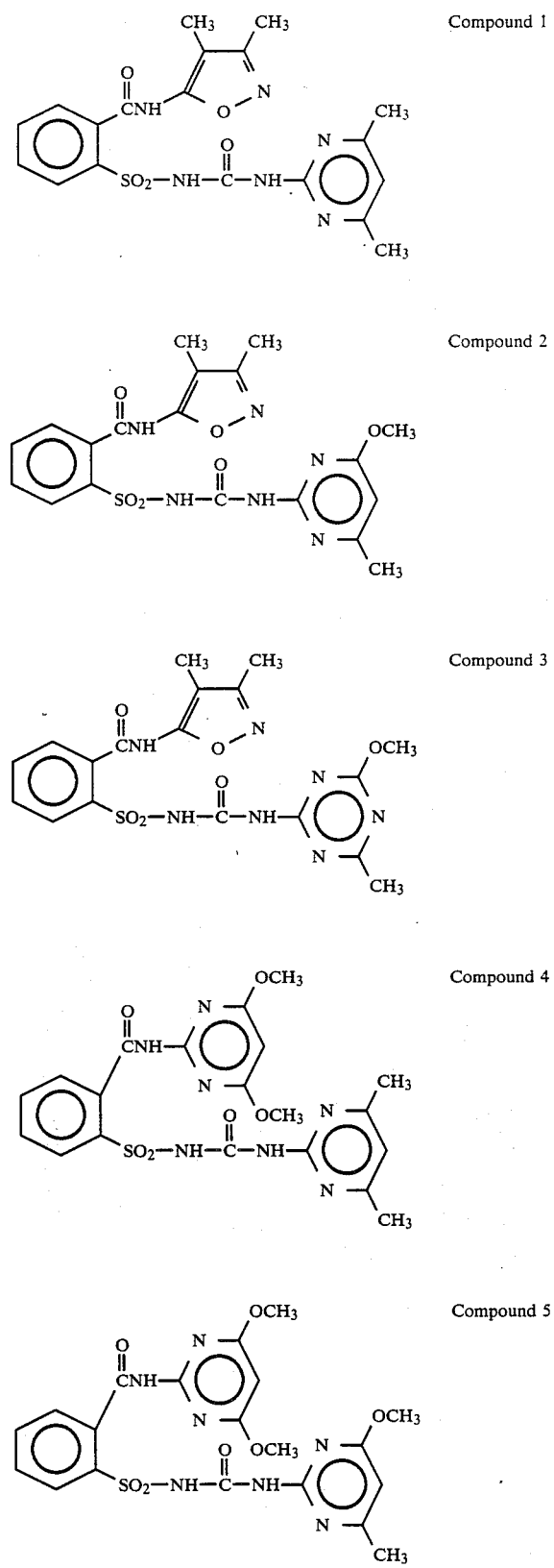

TABLE A-continued

TABLE A-continued
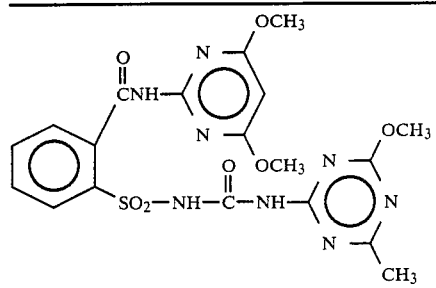
Compound 6
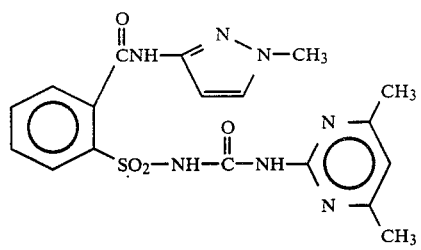
Compound 7
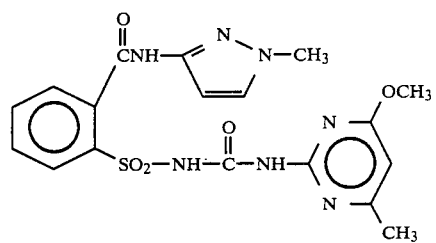
Compound 8
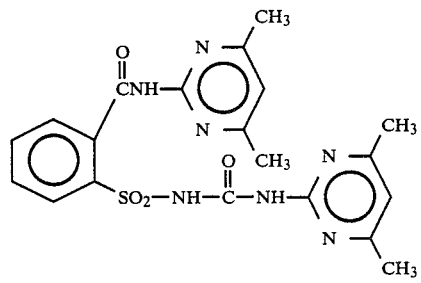
Compound 9
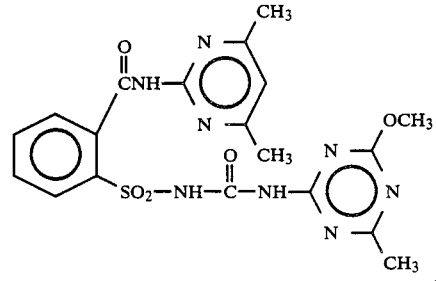
Compound 10
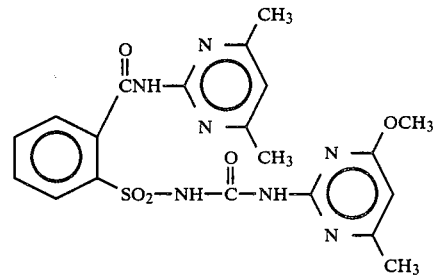
Compound 11
TABLE A-continued
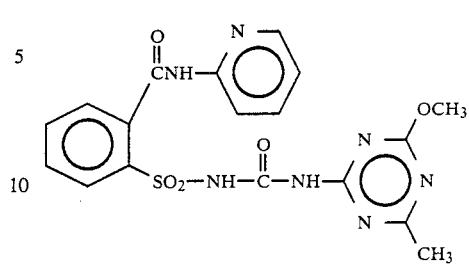
Compound 12
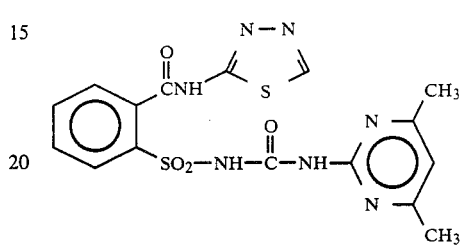
Compound 13
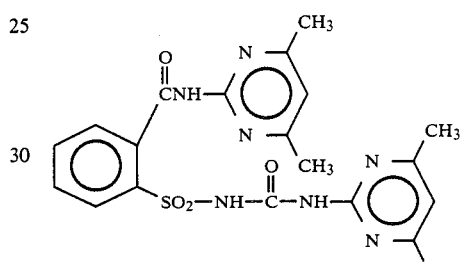
Compound 14
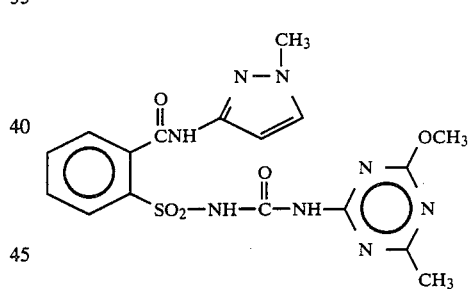
Compound 15
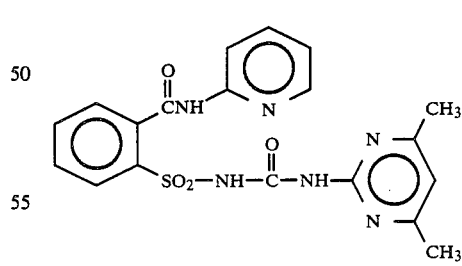
Compound 16
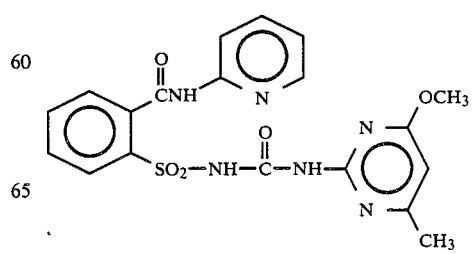
Compound 17

TABLE A-continued

| | | Compound 18 |
|---|---|---|
| 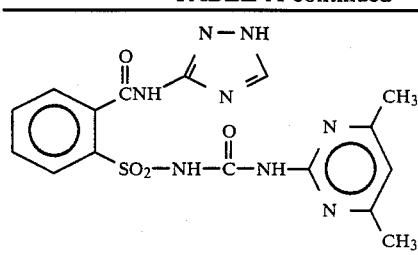 | | |
| 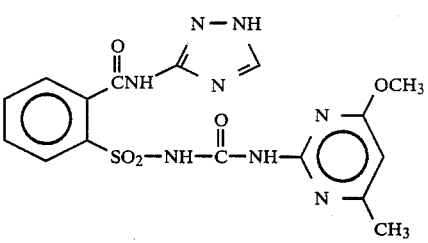 | | Compound 19 |
| 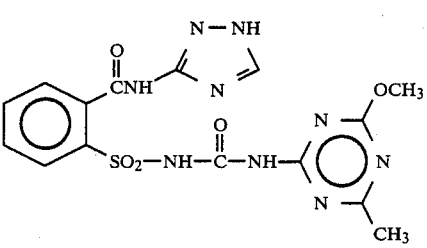 | | Compound 20 |
| 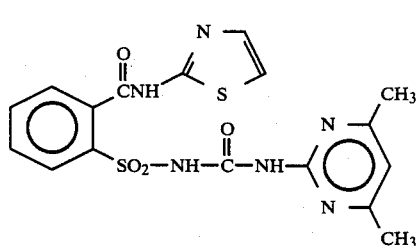 | | Compound 21 |
| 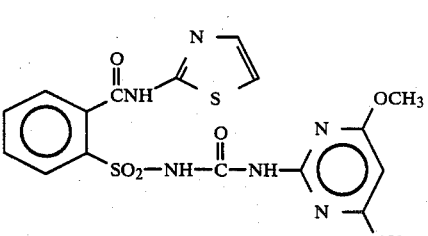 | | Compound 22 |
| 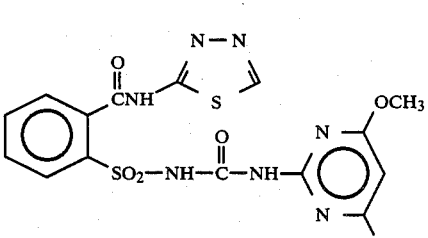 | | Compound 23 |

| | Cmpd. 1 | Cmpd. 2 | Cmpd. 3 | Cmpd. 4 |
|---|---|---|---|---|
| Rate kg/ha | 0.05 | 0.05 | 0.05 | 0.05 |
| POST-EMERGENCE | | | | |
| Bush bean | 2G | 4C,9G,6Y | 0 | 0 |
| Cotton | 1H | 2C,6G | 0 | 2H |
| Morningglory | 2H | 4C,7G | 3G | 1H |
| Cocklebur | 1H | 3C,6G | 0 | 1H |
| Cassia | 0 | 2C | 0 | 0 |
| Nutsedge | 0 | 0 | 0 | 0 |
| Crabgrass | 0 | 0 | 0 | 0 |
| Barnyardgrass | 0 | 5G | 0 | 0 |
| Wild Oats | 0 | 0 | 0 | 0 |
| Wheat | 0 | 0 | 0 | 0 |
| Corn | 0 | 0 | 0 | 0 |
| Soybean | 2C,5G | 1H,2C,6G | 1H | 0 |
| Rice | 0 | 2C | 0 | 0 |
| Sorghum | 0 | 2C | 0 | 0 |
| PRE-EMERGENCE | | | | |
| Morningglory | 0 | 3C,5H | 0 | 1C |
| Cocklebur | 0 | 2C | 0 | 0 |
| Cassia | 0 | 2C | 0 | 0 |
| Nutsedge | 0 | 0 | 0 | 0 |
| Crabgrass | 0 | 2G | 0 | 0 |
| Barnyardgrass | 0 | 1C | 0 | 0 |
| Wild Oats | 0 | 3G | 0 | 0 |
| Wheat | 0 | 2G | 0 | 0 |
| Corn | 0 | 2C | 0 | 1C |
| Soybean | 0 | 2C | 0 | 0 |
| Rice | 0 | 2C | 0 | 0 |
| Sorghum | 0 | 2C,5G | 0 | 0 |

| | Cmpd. 5 | Cmpd. 6 | Cmpd. 7 | Cmpd. 8 |
|---|---|---|---|---|
| Rate kg/ha | 0.05 | 0.05 | 0.05 | 0.05 |
| POST-EMERGENCE | | | | |
| Bush bean | 6C,9G,6Y | 0 | 9C | 9C |
| Cotton | 4C,9G | 0 | 5C,9G | 4C,9G |
| Morningglory | 2C,8G | 0 | 2C,5G | 2C,9H |
| Cocklebur | 2H,4G | 0 | 2C,9G | 1C,9H |
| Cassia | 2C,5G | 0 | 5C,9G | 5C,9G |
| Nutsedge | 1C,9G | 0 | 9G | 2C,9G |
| Crabgrass | 1C,5G | 0 | 2C,9G | 2C,8G |
| Barnyardgrass | 9H | 0 | 5C,9G | 5C,9H |
| Wild Oats | 6G,5X | 0 | 9G | 2C,9G |
| Wheat | 6G | 0 | 2C,9G | 1C,9G |
| Corn | 3U,9H | 0 | 5U,9G | 2U,9H |
| Soybean | 4C,9G | 0 | 9C | 9C |
| Rice | 4C,9G | 0 | 5C,9G | 5C,9G |
| Sorghum | 2C,9G | 0 | 3C,9G | 2C,9G |
| PRE-EMERGENCE | | | | |
| Morningglory | 8G | 0 | 9G | 9H |
| Cocklebur | 9H | 0 | 9G | 9H |
| Cassia | 5G | 0 | 7G | 8G |
| Nutsedge | 10E | 0 | 10E | 9G |
| Crabgrass | 3C | 0 | 5G | 5G |
| Barnyardgrass | 2C,9H | 0 | 2C,9H | 3C,9H |
| Wild Oats | 2C,7G | 0 | 2C,8G | 2C,8G |
| Wheat | 1C,8G | 0 | 9H | 1C,9G |
| Corn | 3C,8G | 0 | 3C,9G | 3C,9G |
| Soybean | 1C,5H | 0 | 7H | 2C,7H |
| Rice | 9H | 0 | 10E | 10E |
| Sorghum | 1C,8G | 0 | 5C,9H | 2U,9G |

| | Cmpd. 9 | Cmpd. 10 | Cmpd. 11 | Cmpd. 12 |
|---|---|---|---|---|
| Rate kg/ha | 0.05 | 0.05 | 0.05 | 0.05 |
| POST-EMERGENCE | | | | |
| Bush bean | 0 | 6C,9G,6Y | 5C,9G,6Y | 4S,8G,6Y |
| Cotton | 0 | 5C,9G | 1U,4C,9G | 2C,7G |
| Morningglory | 0 | 5C,9G | 1C,3G | 1C,6G |
| Cocklebur | 0 | 1H | 2C,8G | 0 |
| Cassia | 0 | 2C | 1C,5G | 2C |
| Nutsedge | 4G | 1C | 5C,9G | 0 |
| Crabgrass | 1C,5G | 0 | 2C,8G | 0 |
| Barnyardgrass | 1C,5G | 0 | 6C,9H | 0 |
| Wild Oats | 0 | 0 | 1C,8G | 0 |
| Wheat | 0 | 0 | 5C,9G | 0 |
| Corn | 1C,4G | 2C,6H | 5U,9G | 0 |
| Soybean | 1H | 2C,7G | 3C,9G | 1C,1H |
| Rice | 1C,5G | 0 | 9C | 0 |
| Sorghum | 1C,9G | 1C,8H | 9C | 0 |
| PRE-EMERGENCE | | | | |
| Moringglory | 0 | 9G | 9G | 4G |

TABLE A-continued

| | Cmpd. 13 | | |
|---|---|---|---|
| Cocklebur | 9H | 9H | 9H | 5H |
| Cassia | 1C | 1C | 1C,5G | 0 |
| Nutsedge | 2G | 0 | 8G | 0 |
| Crabgrass | 0 | 0 | 1C,5G | 0 |
| Barnyardgrass | 2G | 1C | 1C,9H | 0 |
| Wild Oats | 2G | 0 | 1C,8G | 0 |
| Wheat | 2G | 0 | 9G | 0 |
| Corn | 1C,6G | 1C,6G | 1U,9G | 1C |
| Soybean | 0 | 1C,2H | 2C,6H | 1H |
| Rice | 1C,3G | 1C,3G | 9H | 0 |
| Sorghum | 1C,5H | 1C,5G | 1C,9G | 0 |

| | Cmpd. 13 | Cmpd. 14 | Cmpd. 15 |
|---|---|---|---|
| Rate kg/ha | 0.05 | 0.4 | 0.05 |
| POST-EMERGENCE | | | |
| Bush bean | 9C | 8D,9G,6Y | 9C |
| Cotton | 4C,9G | 9G | 2U,3C,9G |
| Morningglory | 2C,5G | — | 10C |
| Cocklebur | 4C,9G | 4G | 2C,8G |
| Cassia | 6G | 9G | 6C,9G |
| Nutsedge | 9G | 9G | 2C,4G |
| Crabgrass | 2C,8G | 5G | 2C |
| Barnyardgrass | 3C,9H | — | 2C |
| Wild Oats | 2C,9G | — | 1C |
| Wheat | 2C,9G | 9G | 1C |
| Corn | 5U,9G | 9C | 3C,9H |
| Soybean | 6C,9G | 9G | 9C |
| Rice | 6C,9G | 9G | 2C,7G |
| Sorghum | 2U,9G | 9C | 3C,8H |
| PRE-EMERGENCE | | | |
| Morningglory | 9G | 9G | 9G |
| Cocklebur | 9H | — | 9H |
| Cassia | 6G | 9G | 3C,9G |
| Nutsedge | 10E | 10E | 10E |
| Crabgrass | 2C,8G | 2C,8G | 3G |
| Barnyardgrass | 2C,9H | 3C,9G | 2C,4G |
| Wild Oats | 1C,9G | 1C,8G | 1C |
| Wheat | 9G | 1C,9G | 0 |
| Corn | 2C,9G | 1U,9G | 2C,6G |
| Soybean | 6H | 9H | 2C,4H |
| Rice | 10E | 10E | 2C,5H |
| Sorghum | 5C,9H | 9H | 2C,7G |

| | Cmpd. 16 | Cmpd. 17 | Cmpd. 18 | Cmpd. 19 |
|---|---|---|---|---|
| Rate kg/ha | 0.05 | 0.05 | 0.05 | 0.05 |
| POST-EMERGENCE | | | | |
| Bush bean | 5C,9G,6Y | 9C | 10D,9G | 9D,9G,6Y |
| Cotton | 3C,9G | 4C,8G | 2U,5C,9G | 2C,3H,9G |
| Morningglory | 5G | 2C,8G | 2C | 1C,4G |
| Cocklebur | 6G | 4G | 5C,9G | 2G |
| Cassia | 4G | 2G | 5C,8G | 2C,4G |
| Nutsedge | 2C,9G | 8G | 9G | 7G |
| Crabgrass | 1C,9G | 5G | 1C,9G | 5G |
| Barnyardgrass | 2C,9H | 3C,9H | 2C,9H | 5C,9H |
| Wild Oats | 9G | 1C,5G | 1C,9H | 5G |
| Wheat | 9G | 1C,5G | 9G | 6G |
| Corn | 1C,9G | 2C,9H | 3U,9G | 2C,9H |
| Soybean | 2C,7H | 2C,9G | 5C,9G | 2C,8G |
| Rice | 9G,5I | 2C,9G | 4C,9G | 1C,9G |
| Sorghum | 9G,5I | 1C,9G | 5U,9G | 9G |
| PRE-EMERGENCE | | | | |
| Morningglory | 9G | 9G | 9G | 9G |
| Cocklebur | 9H | 9H | 9H | 9H |
| Cassia | 7G | 8G | 8G | 8G |
| Nutsedge | 10E | 10E | 10E | 9G |
| Crabgrass | 3C,7G | 1C,5G | 1C,5G | 2C,4G |
| Barnyardgrass | 2C,9G | 5C,9H | 3C,9H | 9C |
| Wild Oats | 9G | 1C,9G | 2C,9G | 2C,9G |

TABLE A-continued

| | Cmpd. 16 | Cmpd. 17 | Cmpd. 18 | Cmpd. 19 |
|---|---|---|---|---|
| Wheat | 9G | 9G | 9G | 1C,9G |
| Corn | 3C,9G | 2C,9G | 9G | 1C,9G |
| Soybean | 7H | 8H | 9H | 1C,5G |
| Rice | 10E | 10E | 10E | 10E |
| Sorghum | 5C,9H | 2U,9G | 6C,9H | 2U,9G |

| | Cmpd. 20 | Cmpd. 21 | Cmpd. 22 | Cmpd. 23 |
|---|---|---|---|---|
| Rate kg/ha | 0.05 | 0.05 | 0.05 | 0.05 |
| POST-EMERGENCE | | | | |
| Bush bean | 9C | 6C,9G | 9C | 7C,9G |
| Cotton | 2U,5C,9G | 6C,9G | 6C,9G | 4C,9G |
| Morningglory | 2C,8G | 2C | 9C | 3C,5G |
| Cocklebur | 2G | 4C,9G | 5C,9G | 1C,4G |
| Cassia | 4C,6G | 1C,3G | 5C,9G | 2C |
| Nutsedge | 0 | 5C,9G | 8G | 2C,8G |
| Crabgrass | 0 | 3C,9G | 2C,8G | 2C,8G |
| Barnyardgrass | 0 | 9C | 10C | 3C,9H |
| Wild Oats | 0 | 9G | 9G | 4C,9G |
| Wheat | 0 | 4C,9G | 5C,6G | 2C,8G |
| Corn | 1C,5H | 5U,9G | 5U,9C | 2C,9H |
| Soybean | 2C,9G | 6C,9G | 9C | 6C,9G |
| Rice | 4G | 2C,9G | 5C,9G | 2C,9G |
| Sorghum | 2C,9G | 5C,9G | 9C | 2C,9G |
| PRE-EMERGENCE | | | | |
| Morningglory | 9G | 9G | 9G | 9G |
| Cocklebur | 7H | 9H | 9H | 8H |
| Cassia | 7G | 8G | 9G | 7G |
| Nutsedge | 0 | 10E | 10E | 10E |
| Crabgrass | 1C | 1C,7G | 2C,8G | 5G,1C |
| Barnyardgrass | 1C | 4C,9H | 5C,9H | 2C,9G |
| Wild Oats | 0 | 2C,8G | 2C,9H | 2C,8G |
| Wheat | 0 | 1C,9H | 2C,9H | 2C,9G |
| Corn | 1C,4G | 10E | 9G | 8G |
| Soybean | 1C,3G | 5H | 9H | 2C,6H |
| Rice | 2C,4G | 10E | 10E | 4C,9H |
| Sorghum | 2C | 5C,9H | 5C,9H | 9G |

Test B

Two plastic bulb pans were filled with fertilized and limed Fallsington silt loam soil. One pan was planted with corn, sorghum, Kentucky bluegrass and several grassy weeds. The other pan was planted with cotton, soybeans, purple nutsedge (*Cyperus rotundus*), and several broadleaf weeds. The following grassy and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pensylvanicum*), pigweed (*Amaranthus retroflexus*), morningglory (*Ipomoea hederacea*), cassia (*Cassia tora*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugarbeets. The above four containers were treated pre-emergence with several test compounds within the scope of the invention.

Twenty-eight days after treatment, the plants were evaluated and visually rated for response to the chemical treatments utilizing the rating system described previously for Test A. The data are summarized in Table B. Note that certain compounds have relative tolerance for wheat.

TABLE B

PRE-EMERGENCE ON FALLSINGTON SILT LOAM

| | Compound 5 | Compound 7 | Compound 8 | Compound 11 | Compound 13 | Compound 16 | Compound 17 |
|---|---|---|---|---|---|---|---|

TABLE B-continued

| | PRE-EMERGENCE ON FALLSINGTON SILT LOAM | | | | | | | | | | | | | |
|---|---|---|---|---|---|---|---|---|---|---|---|---|---|
| Rate kg/ha | .060 | .250 | .030 | .120 | .030 | .120 | .060 | .250 | .030 | .120 | 0.25 | 0.0625 | 0.25 | 0.0625 |
| Crabgrass | 0 | 0 | 0 | 4G,2H | 0 | 4G | 0 | 6G | 0 | 3G | 8G,3H | 7G,3H | 6G,3H | 5G,2H |
| Barnyardgrass | 4C,6G | 5C,7G | 5G,3H | 7G,5H | 6G,2H | 8G,6C | 7G,5H | 9G,9C | 3G | 5G | 8G,9C | 8G,8C | 8G,8C | 7G,5C |
| Sorghum | 7G,5H | 8G,5H | 8G,5H | 10C | 6G,3H | 8G | 8G,8C | 10C | 5G,3H | 9G,9C | 10E | 10C | 9C,9G | 7G,5H |
| Wild Oats | 5G | 6G,3H | 5G | 7G | 5G | 7G | 7G,3H | 7G,6C | 4G | 6G,3H | 6G,3C | 6G,3H | 6G,3H | 5G |
| Johnsongrass | 3G | 7G,3H | 7G,5H | 7G,5H | 4G,3H | 7G,3H | 6G,3H | 7G,5H | 4G | 7G,5H | 8G,5H | 5H,7G | 7G,5H | 3H,4G |
| Dallisgrass | 0 | 4G | 2G | 5G | 0 | 4G | 6G | 8G,3H | 2G | 6G | 7C,8G | 8G,3H | 6G | 5G |
| Giant foxtail | 0 | 7G,5H | 2G | 5G,3H | 4G,3H | 7G,3H | 7G,5H | 9G,5H | 0 | 3G,2H | 8G,9C | 7G,5C | 7G,6C | 6G,3C |
| Ky. bluegrass | 5G,3H | 6G,3H | 6G,3H | 6G,3H | 5G | 6G,3H | 7G,7C | 8G,8C | 6G | 7G | 8G,8C | 8G,7C | 8G,8C | 7G |
| Cheatgrass | 8G,8C | 10C | 7G | 7G | 6G | 7G,5E | 8G,8C | 10E | 8G | 8G | 10C | 10C | 7G,8C | 10C |
| Sugarbeets | 7G,8C | 9G,9C | 8G,8C | 9G,9C | 8G,7C | 9G,9C | 7G,8C | 9G,9C | 6G,4C | 8G,8C | 8G,9C | 8G,8C | 8G,8C | 8G,8C |
| Corn | 0 | 8G,5H | 7G,5H | 10C | 3G | 6G,3H | 3H | 7G,5H | 3G | 3G | 9G,9C | 9G,9C | 5G,5H | 3G |
| Mustard | 10C | 10C | 8G,6C | 9G,9C | 8G,8C | 9G,9C | 9G,8C | 10C | 7G,6C | 9G,9C | 10C | 8G,8C | 9G,9C | 8G,8C |
| Cocklebur | 5G | 5G,3H | 6G | 7G,5H | 3G | 7G | 3G | 6G,3H | 6G,5C | 6G,2C | 7G | 5G | 6G | 3G |
| Pigweed | 6G,5C | 8G,8C | — | — | — | — | 9G,9C | 10C | — | — | 10C | 10C | 9G,9C | 10C |
| Nutsedge | 9G | 8G | 10E | 10E | 0 | 10E | 3G | 10E | 9G | 10E | 10E | 8G | 3G | 3G |
| Cotton | 8G,5C | 7G | 8G,8C | 9G,9C | 0 | 8G,8C | 2G | 9G,8C | 7G,3H | 8G,5H | 9G | 7G | 7G | 6G |
| Morningglory | 7G | 8G | 5G | 7G | 0 | 8G | 5G | 8G,5C | 7G | 8G | 9G,5C | 7G,3C | 9G,8C | 5G |
| Cassia | 8G,3C | 7G,3C | 5G | 5G | 0 | 7G | 4G,3C | 7G,3C | 5G | 7G,5C | 6G | 3G | 7G | 5G |
| Teaweed | 4G | 4G | 0 | 5C,7G | 0 | 7G,3C | 4G | 6G | 4G | 7G,4C | 6G,3C | 3G | 5G | 0 |
| Velvetleaf | 6G,3H | 7G,6C | 8G,5H | 9G,9C | 6G,5H | 10C | 8G,8H | 8G,7C | 6G,3H | 7G,5H | 9G,5H | 8G,5H | 6G,3H | 5G,3H |
| Jimsonweed | 4G,4C | 7G,6C | 0 | 5G,3C | 0 | 5G,5C | 5G,3C | 7G,5C | 0 | 3G,3C | 6G,3C | 4G | 6G,4C | 3G,4C |
| Soybean | 4G,3H | 6G,3H | 4G | 7G,5H | 4G | 8G,8C | 3G,2C | 9G,8C | 3G,3H | 5G,3H | 7G,5H | 4G,1C | 5H,7G | 5G,2H |
| Rice | 7G,5H | 10C | 10E | 10E | 7G | 10E | 8G,8C | 10C | 9G,9C | 10C | 10E | 10E | 7G,5H | 7G,5H |
| Wheat | 4G | 5G | 4G | 7G,3H | 3G | 6G,3H | 4G | 7G,5C | 3G | 4G | 7G,3C | 6G,2C | 5G | 4G |

| | Compound 18 | | Compound 19 | | Compound 20 | | Compound 21 | | Compound 22 | | Compound 23 | | Compound 14 | |
|---|---|---|---|---|---|---|---|---|---|---|---|---|---|---|
| Rate kg/ha | 0.12 | 0.0312 | 0.12 | 0.0312 | 0.12 | 0.0312 | 0.12 | 0.0312 | 0.12 | 0.0312 | 0.12 | 0.0312 | 0.25 | 0.06 |
| Crabgrass | 6G | 5G | 3G | 0 | 0 | 0 | 7G | 4G | 5G | 3G | 0 | 0 | 3H | 0 |
| Barnyardgrass | 8G,8C | 8G,3C | 7G,5C | 5G,2C | 0 | 0 | 8G | 5G | 8G,3H | 6G,2H | 5G | 0 | 5G,3H | 0 |
| Sorghum | 10C | 9G,9C | 7G,3H | 6G,3H | 3G | 0 | 10C | 7G,3H | 9G,9C | 9G,3H | 7G,5H | 2G | 8G,5H | 5G,5H |
| Wild Oats | 6G,6C | 6G,3C | 6G,2H | 4G | 0 | 0 | 7G | 4G | 7G,3H | 4G | 4G | 0 | 4G | 0 |
| Johnsongrass | 8G,8C | 8C,8G | 7G,5H | 4G,3H | 0 | 0 | 7G | 3G | 8G | 7G | 3G | 0 | 6G,3H | 0 |
| Dallisgrass | 3H,8G | 7G,3H | 4G | 3G | 0 | 0 | 5G | 0 | 5G | 2G | 3G | 0 | 0 | 0 |
| Giant foxtail | 8G,5H | 8G,5H | 6G,3H | 4G | 0 | 0 | 5G,3H | 0 | 8G,5H | 4G | 3G | 0 | 0 | 0 |
| Ky. bluegrass | 7G,8C | 7G,8C | 6G | 5G | 3G | 0 | 6G | 5G | 6C,6G | 5G | 5G | 0 | 8G,8C | 5G,5H |
| Cheatgrass | 10E | 10E | 7G,8C | 6G | 0 | 0 | 9G,9C | 7G | 10E | 5G | 0 | 0 | 3G,3H | 3G |
| Sugarbeets | 9G,9C | 7G,7C | 8G,8C | 6G,5C | 8G,8C | 8G,8C | 7G,7C | 6G,5H | 8G,8C | 6G,3H | 7G,6C | 4G | 7G,8C | 6G,7C |
| Corn | 10E | 10E | 8C,8G | 4G | 2G | 0 | 6G,5H | 0 | 4G | 0 | 0 | 0 | 3G, | 0 |
| Mustard | 10C | 8G,5C | 9G,8C | 5C,8G | 7G,5C | 5G | 9G,9C | 8G,8C | 9G,9C | 8G,8C | 9G,9C | 6G,5C | 9G,9C | 6G,5E |
| Cocklebur | 8G,5C | 6G | 6G | 5G | 6G | 7G | 5G,3H | 5G | 2G | — | 3G | 0 | 4G | 0 |
| Pigweed | 10C | 7G | 7G,6C | 3G | 6G | 0 | — | — | — | — | — | — | 10C | 7G,9E |
| Nutsedge | 10E | 10E | 7G | 5G | 3G | 0 | 10E | 2G | 3G | 0 | 7G | 0 | 3G | 0 |
| Cotton | 9G,5H | 9G,5H | 3H,6G | 0 | 9G,3H | 7G,3H | 3H,7G | 3G | 5G,5H | 4G,3H | 3G | 0 | 8G | 2G |
| Morningglory | 8G,5C | 7G,3C | 7G,5H | 3G | 8G,3H | 5G | 7G,3H | 3H | 3G | 4G | 3G | 3G | 8G | 4G |
| Cassia | 5G | 5G | 4G | 3G | 5G | 4G | 7G,3C | 3G | 6G | 6G | 5G | 0 | 8G | 0 |
| Teaweed | 7G | 5G | 4G | 3G | 3G | 2G | 10E | 3G | 6G,3C | 4G | 2G | 0 | 5G | 0 |
| Velvetleaf | 9G,5C | 8G,3H | 6G,5H | 4G,3H | 2G | 3G | 7G,8C | 5G,3H | 5G,5H | 4G,3H | 5G,3H | 0 | 6G | 0 |
| Jimsonweed | 9G,8C | 5G,3C | 5G | 2G | 4G | 3G | 6G,3C | 4G | 4G,3C | 3G | 3G | 0 | 7G,7C | 0 |
| Soybean | 8G,5H | 7G,5H | 6G,5H | 2H | 5G,1C | 2G | 5G,3H | 2G | 3G | 4G | 2G | 0 | 0 | 0 |
| Rice | 10E | 10E | 7G | 5G | 0 | 0 | 10E | 10E | 10E | 7G | 7G,7C | 3G | 8G,3H | 6G |
| Wheat | 7G | 7G,3C | 4G | 2G | 0 | 0 | 4G | 0 | 3G | 3G | 2G | 0 | 36 | 0 |

Test C

Twenty-five cm diameter plastic pots filled with Fallsington silt loam were planted with soybeans, cotton, alfalfa, corn, rice, wheat, sorghum, velvetleaf (*Abutilon theophrasti*), sesbania (*Sesbania exaltata*), Cassia (*Cassia tora*), morningglory (*Ipomoea hederacea*), jimsonweed (*Datura stramonium*), cocklebur (*Xanthium pensylvanicum*), crabgrass (Digitaria sp.), nutsedge (*Cyperus rotundus*), barnyardgrass (*Echinochloa crusgalli*), giant foxtail (*Setaria faberii*) and wild oats (*Avena fatua*). Approximately 2½ weeks after planting, the young plants and the soil around them were sprayed overall with the test chemicals dissolved in a non-phytotoxic solvent. Two weeks after treatment, all species were compared to untreated controls and visually rated for response to treatment. The rating system was as described previously for Test A. The data are presented in Table C. Note that one compound is especially tolerant to alfalfa.

TABLE C
POST-EMERGENCE
Over-the-Top Soil/Foliage Treatment

| | Compound 5 | | Compound 7 | | Compound 8 | | Compound 11 | | Compound 13 | | Compound 15 | | Compound 16 | | Compound 17 | |
|---|---|---|---|---|---|---|---|---|---|---|---|---|---|---|---|---|
| Rate kg/ha | 0.06 | 0.0125 | 0.06 | 0.0125 | 0.06 | 0.125 | 0.06 | 0.125 | 0.006 | 0.06 | 0.125 | 0.06 | 0.125 | 0.063 | .016 | .250 | .063 |
| Soybeans | 10G,7C | 8G,5C | 10G,8C | 10G,3C | 9G,6C | 10G,5C | 10C | 8G,5C | 2C | 9G,2C | 5G | 10G,7C | 10G,3C | 8G | 8G | 9G | 6G |
| Velvetleaf | 9G,8C | 6G | 10C | 9G | 10C | 7G | 10C | 10C | 0 | 9G,4C | 2G,2C | 9G,8C | 5G,2C | 9G,7C | 8G,4C | 9G,8C | 7G,5C |
| Sesbania | 9G,3C | 7G | 9G,3C | 8G | 10C | 8G | 10C | 10C | 4G | 8G | 2G | 9G,9C | 5G | 8G | 7G,5C | 9G,7C | 7G,2C |
| Cassia | 9G,3C | 3G | 8G | 4G | 10G | 5C | 9G,9C | 9G,9C | 2C | 2C | 2G | 9G,8C | 9G,6C | 2C | 3G,2C | 8G,3C | 9G,7C |
| Cotton | 8G | 6G | 10G | 7G | 10C | 5C | 9G,9C | 9G,9C | 5G | 8G | 2G | 9G,5C | 8G,3C | 6G | 2G | 8G,3C | 7G,2C |
| Morningglory | 9G | 3G | 9G,6C | 8G | 9G,5C | 9G,5C | 9G,9C | 10C | 4G | 9G | 10G | 9G,5C | 7G | 2C | 0 | 8G,7C | 8G,7C |
| Alfalfa | 9G,5C | 2G | 6G | 9G | 8G,3C | 8G | 10C | 9G,2C | 5G | 3G | 2C | 10C | 9G | 2C | 2C | 10C | 8G,7C |
| Jimsonweed | 0 | 0 | 9G | 0 | 6G,3C | 8G | 10C | 10C | 6G | 0 | 4G | 9G,5C | 4G | 5G | 5G | 7G | 8G |
| Cocklebur | 0 | 0 | 8G | 5G | 9G | 7G | 9G | 6G | 2C | 5G | 0 | 8G | 2G | 8G | 7G | 8G | 8G |
| Sunflower | 4G | 0 | 8G,2H | 6G | 8G,2H | 5G | 9G,2C | 7G | 2C | 4G | 4G | 10C | 6G,2H | 5G | 7G | 8G,6C | 4G,4C |
| Mustard | 9G | 9G | 9G,9C | 9G | 9G,5C | 9G | 10C | 10C | 3G | 9G | 7G | 10C | 8G | 10C | 10C | 9G,9C | 9G,9C |
| Sugarbeets | 8G | 5G,3G | 8G | 9G | 9G,5C | 5G | 10C | 9G,4C | 4G | 9G | 4G | 10C | 5G | 9G | 9G | 9G,5C | 9G,5C |
| Corn | 8G,3U | 8G,3U | 9G,9U | 9G,9C | 10C | 9G,8C | 9G,9C | 9C,3C | 4G | 8G,3U | 8G,1H | 9G,9C | 6G | 9G,5C | 9G,5C | 10C | 9G,9C |
| Crabgrass | 0 | 4C | 4G | 0 | 2G | 0 | 2G | 2G | 6G,3H | 2G | 0 | 7G,3U | 6G | 10C | 7G | 6G,3C | 2G |
| Rice | 4G,2C | 4G | 7G,3C | 7G,3C | 10C | 4G | 10C | 9G,8C | 4G | 8G | 8G | 10C | 8G | 7G,4C | 7G,1C | 9G,8C | 7G |
| Nutsedge | 8G | 9C | 7G | 9C | 6G | 3G,3C | 6G | 9G,9C | 4G | 8G,7C | 7G | 10C | 4G | 6G | | 10C | 9C |
| Barnyardgrass | 9G,9C | 5G | 9G,9C | 8G,8C | 10C | 8G | 9G,2H | 9G,2U | 1G | 9G,2H | 6G | 10C | 3G | 9G,4C | 10C | 9G,8C | 8G |
| Wheat | 0 | 0 | 9G,2C | 5G | 5G,2C | 3G | 7G,5U | 9G,9C | 3G | 7G,3C | 5G | 9G,9C | 2G | 8G,2C | 8G,4C | 9G,4C | 9G,2C |
| Giant foxtail | 0 | 0 | 8G | 4G | 9G | 5G | 9G,2U | 10C | 2G | 6G | 0 | 9G | 0 | 8G | 8G | 8G,3C | 8G |
| Wild Oats | 4G,4C | 2C | 9G,9C | 7G | 9G,8C | 2G | 10C | 7G,2C | 4G | 7G,3C | 6G,2C | 10C | 6G | 9G | 8G,5C | 9G,4C | 8G |
| Sorghum | 7G | 6G | 8G,8C | 7G,2U | 10C | 6G | 10C | 8G,6C | 4G | 7G | 7G | 10C | 3G | 10C | 8G,8C | 8G,9C | 8G,8C |
| Johnsongrass | 5G | 5G | 9G,8C | 9G,2U | 9G,8C | 9G,3U | — | 5G | 5G | 9G,2U | 4G | 10C | 2G | 9G,7U | 8G,7U | 9G,8C | 7G,3U |
| Field Bindweed | 5G | 4G | 7G | 0 | 7G | 6G | — | 2C | 2C | 10C | 2G | 8G | | 5G | — | 5G | 2G |

| | Compound 17 | Compound 18 | | Compound 21 | | Compound 22 | | Compound 23 | |
|---|---|---|---|---|---|---|---|---|---|
| Rate kg/ha | .016 | 0.0125 | 0.006 | 0.06 | 0.0125 | 0.06 | 0.006 | 0.06 | 0.0125 |
| Soybeans | 6G | 8G | 9G | 10C | 10G,5C | 10C | 10G,3C | 10G,6C | 8G,6C |
| Velvetleaf | 7G | 8G | 5G | 9G,8C | 6G | 8G,5C | 7G,2C | 10C | 2G |
| Sesbania | 7G | 2G | 4G | 9G,8C | 6G | 10C | 9G,3C | 10G,6C | 3G |
| Cassia | 6G | 5G,3C | 0 | 8G | 2G | 9G,8C | 5G,3C | 4G | 7G |
| Cotton | 4G | 2G | 1C | 9G | 3G | 8G,2C | 8G,2C | 7G | 7G |
| Morningglory | 8G,5C | 4G | 5G | 9G | 0 | 9G,2C | 8G,2C | 8G | 4G |
| Alfalfa | 6G,3C | 0 | 4G | 9G,5C | 0 | 9G,7C | 8G,2C | 5G | 5G |
| Jimsonweed | 2G | 6G | 8G,2C | 7G | 5G | 9G,5C | 4G | 8G,6C | 0 |
| Cocklebur | 4G | 6G | 0 | 8G | 5G | 9G | 4G | 0 | 0 |
| Sunflower | 6G,2C | 4G | 0 | 8G,1H | 3G | 6G | 5G | 3G | 1G |
| Mustard | 2C | 8G | 5G | 10C | 3G | 5G | 5G | 6G | 8G |
| Sugarbeets | 7G,2C | 8G | 5G | 10C | 8G | 7G | 8G | 6G | 0 |
| Corn | 8G | 8G,8C | 8G,5H | 10C | 9G | 10C | 9G | 5G | 0 |
| Crabgrass | 9G,7C | 4G | 0 | 7G | 9G,7C | 3G | 7G,8C | 9G,5C | 9G,3U |
| Rice | 0 | 9G,5C | 3G,2C | 10C | 7G,7C | 8G,8C | 4G | 2G | 2G |
| Nutsedge | 7G | 10C | 8G,2C | 7G,7C | 5G,5C | 10C | 7G | 10C | 3C |
| Barnyardgrass | 2G | 10C | 4G,2C | 10C | 10C | 10C | 7G,1H | 8G | 5G |
| Wheat | 4G | 9G,6C | 5G | 9G,8C | 5G | 10C | 2G | 10C | 5G |
| Giant foxtail | 2G | 9G | 6G | 9G | 8G | 8G,2C | 3G | 1G | 0 |
| Wild Oats | 7G | 8G | 0 | 9G | 6G | 9G,2C | 4G | 4G | 4G |
| Sorghum | 4G | 9G,5C | 5G | 10C | 7G,3C | 9G,8C | 0 | 6G | 1C |
| Johnsongrass | 7G | 10C | 6G | 10C | 7G,3U | 10C | 7G | 8G,5C | 6G |
| Field Bindweed | 4G | 9G,8C | 6G | 9G,8U | 7G,3U | 10C | 7G,2H | 9G,2U | 7G |
| | 0 | 5G | 0 | 10C | 2G | 6G | 3G | 2G | 2C |

What is claimed is:
1. A compound selected from

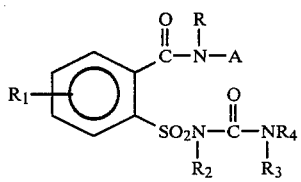

wherein
A is a six-membered aromatic heterocycle, a six-membered dihydroaromatic heterocycle or a six-membered tetrahydroaromatic heterocycle which contains 1-4 hetero-atoms selected from 0-1 oxygen atoms, 0-1 sulfur atoms, and/or 0-4 nitrogen atoms; the heterocycles may be optionally substituted with 1-4 $CH_3$, 1-3 $OCH_3$, 0-1 $SCH_3$, 0-1 Cl, 0-1 $N(CH_3)_2$, or 0-1 CN groups;
R is H or $CH_3$;
$R_1$ is H, F, Cl, Br, $CH_3$, $OCH_3$, $CF_3$ or $NO_2$;
$R_2$ is H or $CH_3$;
$R_3$ is H or $CH_3$;
$R_4$ is

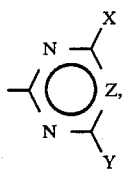

X is $CH_3$, $OCH_3$ or Cl;
Y is H, $CH_3$, $C_2H_5$, $OCH_3$, $OC_2H_5$, $CH_2OCH_3$, $NH_2$, $NHCH_3$ or $N(CH_3)_2$; and
Z is N; provided that
(1) the bond between N—R and A is attached to to a nitrogen or carbon atom of A.

2. Compounds of claim 1 wherein A is an unsubstituted or substituted six-membered aromatic heterocycle containing one to three nitrogen atoms.

3. Compounds of claim 1 wherein A is an unsubstituted or substituted six-membered dihydroaromatic heterocycle containing two nitrogen atoms.

4. Compounds of claim 1 wherein A is an unsubstituted or substituted six-membered tetrahydroaromatic heterocycle containing one nitrogen atom and optionally one heteroatom selected from nitrogen, oxygen or sulfur.

5. Compounds of claim 4 wherein Y is $CH_3$ or $OCH_3$.

6. Compounds of claim 5 wherein A is unsubstituted or optionally substituted with 0-4 $CH_3$ or 0-2 $OCH_3$ groups.

7. Compounds of claim 6 wherein A is a pyridine, a pyrimidine or a 1,3,5-triazine.

8. Compounds of claim 6 wherein A is a tetrahydropyrimidine, a tetrahydro-1,2-oxazine, a tetrahydro-1,3-oxazine, or a tetrahydro-1,3-thiazine.

9. Compounds of claim 7 wherein R, $R_1$, $R_2$ and $R_3$ are H, and A is unsubstituted, or optionally substituted with one methyl group.

10. A composition suitable for controlling the growth of undesired vegetation which comprises an effective amount of a compound of claim 1 and at least one of the following: surfactant, solid or liquid diluent.

11. A composition suitable for controlling the growth of undesired vegetation which comprises an effective amount of a compound of claim 2 and at least one of the following: surfactant, solid or liquid diluent.

12. A composition suitable for controlling the growth of undesired vegetation which comprises an effective amount of a compound of claim 3 and at least one of the following: surfactant, solid or liquid diluent.

13. A composition suitable for controlling the growth of undesired vegetation which comprises an effective amount of a compound of claim 4 and at least one of the following: surfactant, solid or liquid diluent.

14. A method for controlling the growth of undesired vegetation which comprises applying to the locus to be protected an effective amount of a compound of claim 1.

15. A method for controlling the growth of undesired vegetation which comprises applying to the locus to be protected an effective amount of a compound of claim 2.

16. A method for controlling the growth of undesired vegetation which comprises applying to the locus to be protected an effective amount of a compound of claim 3.

17. A method for controlling the growth of undesired vegetation which comprises applying to the locus to be protected an effective amount of a compound of claim 4.

* * * * *